United States Patent
Lange De Oliveira et al.

(10) Patent No.: US 10,338,042 B2
(45) Date of Patent: Jul. 2, 2019

(54) APPARATUS AND METHOD FOR INVESTIGATING DISCONTINUOUS PRODUCT FLUID STREAMS IN THE REACTION OF REACTANT FLUID STREAMS OVER SOLID CATALYSTS

(71) Applicant: hte GmbH the high throughput experimentation company, Heidelberg (DE)

(72) Inventors: Armin Lange De Oliveira, Heidelberg (DE); Nadine Brem, Muehlhausen (DE); Mario Soorholtz, Mannheim (DE); Johannes Lieberknecht, Schwetzingen (DE)

(73) Assignee: hte GmbH the high throughput experimentation company, Heidelberg (DE)

( * ) Notice: Subject to any disclaimer, the term of this patent is extended or adjusted under 35 U.S.C. 154(b) by 109 days.

(21) Appl. No.: 15/028,242

(22) PCT Filed: Oct. 8, 2014

(86) PCT No.: PCT/EP2014/071502
§ 371 (c)(1),
(2) Date: Apr. 8, 2016

(87) PCT Pub. No.: WO2015/052212
PCT Pub. Date: Apr. 16, 2015

(65) Prior Publication Data
US 2016/0252485 A1 Sep. 1, 2016

(30) Foreign Application Priority Data
Oct. 8, 2013 (DE) .................. 10 2013 016 585

(51) Int. Cl.
*G01N 31/10* (2006.01)
*B01J 19/00* (2006.01)
*C40B 30/08* (2006.01)
*C40B 60/12* (2006.01)

(52) U.S. Cl.
CPC .......... *G01N 31/10* (2013.01); *B01J 19/0046* (2013.01); *B01J 2219/00281* (2013.01); *B01J 2219/00286* (2013.01); *B01J 2219/00477* (2013.01); *B01J 2219/00479* (2013.01); *B01J 2219/00704* (2013.01); *B01J 2219/00707* (2013.01); *B01J 2219/00747* (2013.01); *C40B 30/08* (2013.01); *C40B 60/12* (2013.01)

(58) Field of Classification Search
None
See application file for complete search history.

(56) References Cited

U.S. PATENT DOCUMENTS

| 6,551,832 | B1 | 4/2003 | Deves et al. |
| 2003/0040116 | A1 | 2/2003 | Canos et al. |
| 2005/0169815 | A1 | 8/2005 | van den Brink et al. |

FOREIGN PATENT DOCUMENTS

| DE | 10 2004 039 378 A1 | 2/2006 |
| DE | 10 2006 053 078 A1 | 5/2008 |
| DE | 10 2010 050 599 A1 | 6/2011 |
| WO | WO 02/092220 A1 | 11/2002 |
| WO | WO 2004/052530 A1 | 6/2004 |
| WO | WO 2005/063372 A2 | 7/2005 |
| WO | WO 2008/012073 A1 | 1/2008 |
| WO | WO 2012/052149 A2 | 4/2012 |

OTHER PUBLICATIONS

International Preliminary Repot on Patentability and Written Opinion dated Apr. 21, 2016 in PCT/EP2014/071502 filed Oct. 8, 2014.
International Search Report dated May 26, 2015 in PCT/EP2014/071502.

*Primary Examiner* — Paul S Hyun
(74) *Attorney, Agent, or Firm* — Oblon, McClelland, Maier & Neustadt, L.L.P.

(57) ABSTRACT

An apparatus suitable for investigating solid catalysts and processes in which discontinuous fluid streams arise, the apparatus including: a reactant fluid supply point; a reaction space; at least one fluid mixing space; at least one throttle element; at least one pressure control valve; and at least one analyzer. An outlet side of the reaction space is operatively connected to the fluid mixing space via a connecting line and a substream line. The fluid mixing space is connected to the throttle element. The throttle element is operatively connected to the analyzer and an outlet line. The connecting line is operatively connected to the pressure control valve and an exit air line. The pressure control valve is arranged either downstream or upstream of the substream line. When the pressure control valve is upstream of the substream line, the outlet line is provided with a second pressure control valve and a pump.

19 Claims, 21 Drawing Sheets

Figure 8.a
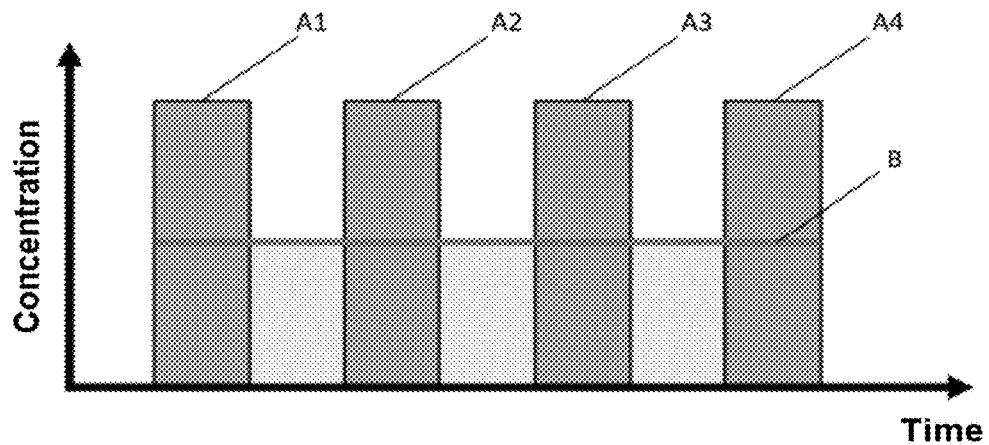
Figure 8.b
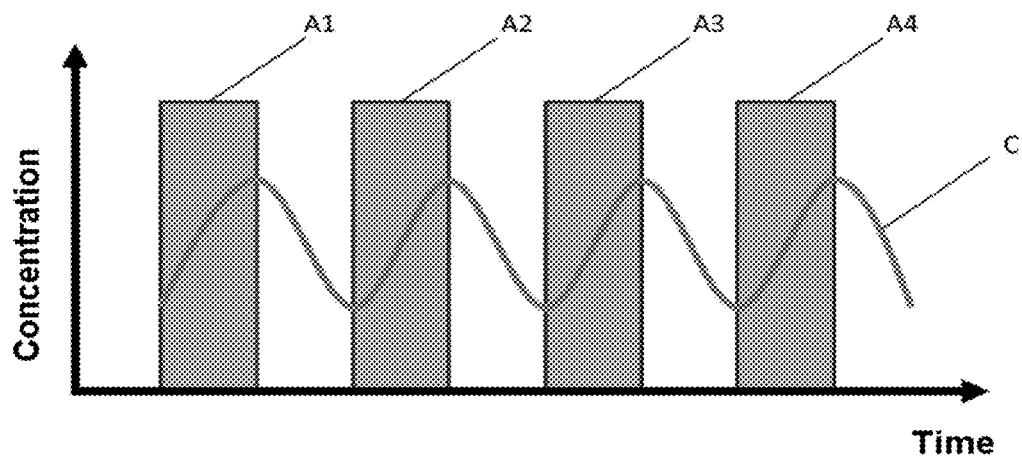

APPARATUS AND METHOD FOR INVESTIGATING DISCONTINUOUS PRODUCT FLUID STREAMS IN THE REACTION OF REACTANT FLUID STREAMS OVER SOLID CATALYSTS

The present invention relates to an apparatus and a method for investigating discontinuous product fluid streams formed on reaction of reactant fluid streams over solid catalysts for example. The product fluid streams formed in catalytic processes may occasionally be subject to marked changes over time, since the catalyst samples to be investigated exhibit aging effects for example or, due to deposits, lose a large part of their activity or completely deactivate within short operating times. Some of the effects of catalyst aging and catalyst deactivation are reversible and the catalysts can be reactivated by means of a suitable regeneration phase. The investigation of catalyst aging and regeneration is of great economic and industrial interest with a view to developing new catalysts and catalytic methods having improved properties. Improving catalytic processes is a major technical challenge in view also of rising energy costs and depletion of raw materials. The development and improvement of high-throughput methods is a central element in catalyst research in order to be able to bring new and improved products to market in shorter units of time.

Laboratory apparatuses for catalyst research which employ gas collection spaces or gas mixing spaces are known in the prior art. Examples include apparatuses which comprise only a single reactor and which are used for investigating FCC catalysts. Coking and deactivation of the catalyst occur in the space of short reaction times in investigations of this type. The reaction products are initially transferred from the reactor into a liquid phase separator to remove the liquid components and subsequently transferred into a gas collection vessel. The gas collection vessels collect the entirety of the process gas, which is subjected to quantitative and qualitative analysis.

That aside, the use of liquid phase separators is also known from the field of catalytic laboratory apparatuses used for high-throughput research. Reference may be made, for example, to WO 2005/063372 of hte Aktiengesellschaft, wherein various designs of catalyst testing apparatuses permitting parallelized investigation of solid catalysts are described. WO2005/063372 shows a number of embodiments of catalyst test apparatuses, wherein every reaction space of the reaction spaces arranged in parallel each has one liquid phase separator per reaction space connected downstream of it. Furthermore, WO2005/063372 discloses in FIG. 6 a catalyst test apparatus, wherein every reaction space is connected to two liquid phase separators each, which liquid phase separators are sequentially arranged and function as high- and low-pressure separators.

WO2004/052530 discloses an apparatus for testing catalysts which is used to generate a multiplicity of fluid streams which are supplied to an analytical characterization process. The individual fluid streams exiting the parallel reaction vessels (8) are initially passed to one gas splitter (12) each. The individual gas splitters (12) are connected to a common multiport valve via lines (12) and pressure reduction elements (18). Moreover, the individual gas splitters (12) comprise connecting lines (14) to a common receptacle (42) in which a separation of liquid and gaseous components is effected. The receptacle (42) is connected via a pressure reduction element (46) to an exit air line (48) and an analysis unit (50) is connected downstream.

DE 1 02 010050599 discloses various apparatuses for testing solid catalysts and for optimizing process parameters. FIG. 5 shows a schematic diagram of an apparatus provided with two reactors arranged in parallel. Every reactor respectively has one separator (4001) connected downstream of it with every separator respectively comprising one outlet for liquids and one outlet for gases.

Reference may further be made to WO 2008/012073 of hte Aktiengesellschaft which was filed on Jul. 24, 2007 and claims priority from Jul. 24, 2006. WO 2008/012073 discloses a catalyst test apparatus which comprises reactors arranged in parallel and which is provided with liquid phase separators and gas collection vessels. WO 2008/012073 relates to the handling of multicomponent mixtures consisting of at least two incompletely miscible fluid phases.

DE 102004039378 discloses an apparatus and a method for controlled taking of samples from pressure vessels, where the vessels can be arranged in parallel. According to the invention, a sample storage unit is located downstream of the pressure vessel and is operatively connected to the pressure vessel via a first valve and to the sample collection unit via a second valve. The invention permits discontinuous taking of samples from the pressure vessel, the sample being transferred to an analysis unit via the sample storage unit.

It is an object of the invention to provide an apparatus and a method permitting investigation of catalytic processes in connection with discontinuous product fluid streams with enhanced time resolution compared to what is possible using the apparatuses and methods known in the prior art. The apparatus according to the invention and the method according to the invention shall, in particular, relate to the investigation of processes having a high tendency to deactivate. The accuracy of the methods known in the prior art for analysis of processes in connection with catalyst deactivation and other time effects should consequently be improved.

Apparatus

The objects mentioned here and further objects are achieved by providing an apparatus for reacting solid catalysts and processes in which discontinuous fluid streams arise, wherein the apparatus comprises a reactant fluid supply point (01), a reaction space (21/1) and at least one fluid mixing space (33), at least one throttle element (11) and at least one pressure control valve (51) at least one analyzer (43), in which apparatus the outlet side of the reaction space (21) is operatively connected to at least one fluid mixing space (33) via a connecting line (22) and a substream line (36) and the at least one fluid mixing space (33) is connected to a throttle element (11), wherein the throttle element (11) is operatively connected to a) an analyzer (43) and b) an outlet line (62); the connecting line (22) is operatively connected to the pressure control valve (51) and an exit air line (63), wherein the pressure control valve (51) is arranged either downstream or upstream of the substream line (36) and, when the pressure control valve (51) upstream of the substream line (36), the outlet line (62) is provided with a second pressure control valve (51/2) and a pump (91).

Preference is also given to an embodiment of the apparatus of the invention, wherein the outlet side of the reaction space (21) is operatively connected via an arrangement composed of connecting line (23), fluid vessel (24), connecting line (25) and a substream line (36) to at least one fluid mixing space (33) and the fluid mixing space (33) is connected to a throttle element (11) wherein the throttle element(s) (11) is or are operatively connected to a) an analyzer (43) and b) an outlet line (62); the connecting line (25) is operatively connected to the pressure control valve (51) and an exit air line (63), wherein the pressure control valve (51) is arranged either downstream or upstream of the substream line (36) and, when the pressure control valve (51) upstream of the substream line (36), the outlet line (62) is provided with a second pressure control valve (51/2) and a pump (91).

In a preferred embodiment, the apparatus according to the invention comprises at least two or more reaction spaces arranged in parallel [(21/1), (21/2), ... (21/x) respectively], every one of the reaction spaces is operatively connected to at least one fluid mixing space (33/x) each, the individual fluid mixing spaces each have one operative connection to a multiway valve (41/1), wherein the multiway valve (41/1) is preferably equipped as a multiport valve and/or a valve (83) is disposed directly upstream of the fluid mixing space (33/x) in the respective operative connection (22) of reaction space (21/x) and fluid mixing space (33/x).

In a preferred embodiment, the apparatus comprises at least four reaction spaces (21/01-21/04), preferably eight reaction spaces (21/01-21/08) and the multiway valve is configured as a multiport valve (41/1).

In a preferred embodiment of the apparatus, every connecting line between the outlet side of a reaction space and the respective gas mixing space (33/x) each comprises one substream line (36/x), the individual substream lines (36/x) are operatively connected to the outlet line (62), wherein the control means (51) is preferably disposed downstream of the connection of the substream lines with the outlet line (62).

In a further and preferred embodiment of the apparatus, every substream line is operatively connected to a second multiport valve (41/2), the multiport valve (41/2) comprises an operative connection to the outlet line (62) and to a second analyzer (43/2), wherein the connection from multiport valve to the outlet line—and also the outlet line of the second analyzer to the outlet line (62)—is upstream of the control means (51). The connection to the outlet line (62) can be configured differently in different embodiments of the apparatus according to the invention. For example, the configuration of the apparatus comprising a multiport valve in the operative connection from the throttle element to the outlet line can also comprise an outlet line (45) which leads from the multiport valve (41) to the outlet line and which bypasses the analyzer (43/1) (as also shown in FIG. 5 for example).

In a preferred embodiment of the apparatus, on the outlet side of the reactor space (21/x) a switching valve (83/x) is operatively connected to the fluid mixing space (33/x) via a substream line (36/x).

Moreover, it is also preferable for the reaction spaces (21/x) to be tubular reactors each having an internal volume in the range of 0.1-5000 mL, preferably of 0.2 mL-200 mL, more preferably of 0.5-100 mL.

In a preferred embodiment of the apparatus (as shown, for example, in FIG. 11), on the outlet side of the reactor space (21/x), a fluid vessel (24/x) is operatively connected to the substream line (36/x). With regard to the dimensions of the fluid vessel (24/x), it is preferable that each displays an internal volume in the range of 5-5000 mL, preferably in the range of 10-3000 mL, more preferably 50-1000 mL. Preferably, the fluid vessels are temperature-controllable, the temperature preferably being in the range of $-20$ to $+400°$ C., preferably in the range from $-10$ to $+350°$ C. and further preferably in the range of $-5$ to $+300°$ C.

In one possible embodiment, the fluid vessel is a condenser which separates condensable fluid components out of the product stream. The fluid vessel can alternatively be designed as a damping vessel or as a condenser and a damping vessel, with the aid of which short-term pressure variations are absorbed. The short-term pressure variations may be caused, for example, by interchange between the fluid phases within a cycle, which can occur when the valves are switched.

With regard to the gas mixing spaces (33/x) it is preferable that these each have an internal volume in the range of 5-5000 mL, more preferably of 10-3000 mL, more preferably of 50-1000 mL. The gas mixing spaces are preferably heatable and are heated at a predetermined temperature and all parallel gas mixing spaces therefore have a defined temperature. It is preferable for all gas mixing spaces to have the same temperature. The temperature of the gas mixing spaces is in the range of 0-400° C., preferably in the range from 0° C. to 350° C. and more preferably in the range of 20-300° C.

When the product fluid streams comprise condensable components prone to condensing out under the conditions prevailing in the gas mixing space, it is advantageous to remove these beforehand using a condenser. A suitable condenser is then preferably disposed in the line system upstream of the gas mixing space (33/x), and a suitable apparatus comprises at least one condenser (24/x) per reactor space (21/x).

In an advantageous embodiment, the apparatus according to the invention comprises at least two sequentially arranged fluid mixing spaces per reaction space and the outlet side of every reaction space (21/x) is operatively connected to the first fluid mixing space (33/x') of this sequential arrangement and the outlet side of the second fluid mixing space (33/x") or the outlet side of the final fluid mixing space of the sequential arrangement is operatively connected to throttle means (11/1) or (11/x).

Useful analyzers include all technical instruments suitable for quantitative and qualitative investigation of material streams. Examples thereof are gas chromatographs, GC-MS, NIR, IR detectors, UV, UV-VIS. When the apparatus is only provided with one analyzer, this can preferably be a GC or a GC-MS. When the apparatus is provided with two or more analyzers it also comprises, for example, at least a hot gas flow analyzer in addition to a GC or a GC-MS.

Determining the activity and the selectivity in respect of a defined target reaction gives the essential parameters for characterizing a catalyst or a catalytic method. The activity is defined as the overall rate at which reactants are consumed. Furthermore, the activity can also be specified in terms of the individual product components formed in a catalytic method. The selectivity is the fraction of a particular product component with respect to the entirety of all product components. Activity and selectivity are time-dependent parameters and regularly change, more or less rapidly, over the course of a method. When changes take place over short time intervals, at present they can be studied only with difficulty with the apparatuses and methods known in the prior art.

In particular embodiments, the apparatus according to the invention can take the form of a riser reactor, a downer reactor, a fixed-bed reactor, a fluidized-bed reactor, an eddy current reactor, an engine test stand or an incineration reactor.

Method

The invention relates to a method for characterizing discontinuous fluid streams, wherein the method comprises the following steps:
  (i) supplying a fluid stream into the interior of a fluid mixing space in a controlled manner, (ii) commixing the fluid stream in the fluid mixing space,
(iii) transferring the commixed fluid stream to a fluid stream outlet by means of a conduit element,
(iv) withdrawing the commixed fluid stream from the conduit element and supplying the substreams to an analysis unit.

It is preferable when carrying out the method when the mean retention time of a molecule or a component in the fluid mixing space corresponds to at least the duration of a single cycle. The mean retention time of a molecule or a component in the fluid mixing space preferably corresponds to the duration T of from two to four cycles when the fluid stream is continuously transferred into the fluid mixing space.

Supplying in a controlled manner may be either continuous supplying in which cyclical fluid streams arise or time limited (i.e. discrete fluid stream packets) supplying in which at least one fluid stream phase which is transferred into the gas mixing vessel by withdrawing substream.

It is preferable when every cycle of the method comprises at least two fluid stream phases following alternately and the at least one fluid stream phase is therefore in each case replaced by at least one second fluid stream phase, wherein the second phase can be replaced by a third fluid stream phase.

The duration of a single cycle in the method according to the invention is preferably in the range from 0.2 to 7200 s, preferably in the range of 1-3600 s.

In a further preferred embodiment of the method, the duration of the reactant stream phase is in the range of 0.1-3600 s, preferably in the range of 0.1-1800 s and more preferably in the range of 0.1-900 s.

The invention permits investigation of processes in connection with discontinuous fluid streams—such as in the investigation of solid catalysts for example—using the apparatus according to the invention and the method is operated in a cyclic mode and every cycle comprises at least two consecutive fluid stream phases having different compositions and/or flow rates of the fluid stream phases.

The method according to the invention can comprise 1-50 fluid stream phases, preferably 2-10 fluid stream phases and more preferably 2-5 fluid stream phases per cycle.

In a specific embodiment of the method carried out using the apparatus shown in FIG. 2, the switching valve ($83/x$) is switched, during one or more fluid stream phases, such that initially one fluid stream and subsequently no fluid stream flows into the gas mixing vessel. The beginning of the additional mixing time is concerned. The gas mixing space ($33/x$) consequently serves as a storage unit for a gas volume of the fluid phases, taking into account the amount of substream withdrawn and the duration of sampling.

Once a suitable total mixing time has been reached, the switching valve ($83/x$) is switched such that a fluid stream, preferably an inert gas and more preferably nitrogen, flows from the gas supply apparatus ($02/x$) into the gas mixing space ($33/x$) downstream of the switching valve ($83/x$) and the fluid volume previously stored in the gas mixing vessel ($33/x$) is flushed out of the gas mixing vessel ($33/x$). This procedure brings about back-mixing of all fluid components for a single fluid stream phase compared to carrying out the method without the switching valve ($83/x$), since a longer retention time of the fluid volume in the gas mixing vessel ($33/x$) is permitted. A correspondingly long retention time needs to be used when carrying out the method according to the invention so that commixing in this way is permitted.

For example, the method according to the invention can comprise at least one reactant stream phase and at least one regeneration stream phase, wherein these follow in alternate operation and therefore the at least one reactant stream phase is in each case replaced by the at least one regeneration phase. A preferred operating mode is notable in that a flushing phase takes place between the reactant stream phase and the regeneration phase. The flushing phase is carried out, for example, by passing an inert gas or a carrier gas containing no reactant or product components through (the reaction space (21) and) the supply line (36) into the fluid mixer (33). The flushing phase makes it technically possible to permit time separation of the reactant stream phase and the regeneration phase and avoid undesired reactions between the reactant stream and the regeneration stream.

The term "mean retention time of molecules or components" relates to the retention times of the molecules or components in the fluid mixer (33).

Supplying a fluid stream means that a channelling connecting element (36) is present which helps to achieve supply of the fluid stream. A characteristic of this supply element (SE) (i.e. element (36)) is the cross sectional area $A_{SE}$ through which the fluid stream passes. Having regard to the time interval $t_1$, the volume $V_{t1}$ passes through the cross sectional area. The fluid mixer (FM) (i.e. element 33) has a cross sectional area $A_{FM}$ which differs from the cross sectional area of the supply element. The flow rate of the fluid stream in the fluid mixer (33) is less than the flow rate of the fluid stream in the supply element (36). Detailed examination shows that the invention relates to supply lines having a diameter in the range from 0.1 to 20 mm, preferably in the range from 0.1 to 10 mm.

The particular design and configuration of the fluid mixing space (33) can be achieved by those skilled in the art using their knowledge of the art. The fluid mixing space permits efficient back-mixing of the fluids.

The characteristic property of a fluid mixer arises from the mean retention times of molecules and components inside the fluid mixer and the duration of a fluid stream phase or of a single fluid stream cycle.

When the fluids are gaseous fluids, the fluid mixer is a gas mixing space ($33/x$). A pipe is the simplest design of such a gas mixing space. It is obvious to those skilled in the art which geometric designs and dimensions of the gas mixing space lead to relatively high back-mixing time constants.

The mean retention time of the molecules and/or components in the gas mixing space (or fluid mixing space) is at least equal to the duration of a fluid stream phase, preferably at least equal to the duration of two fluid stream phases, more preferably at least equal to the duration of three or more fluid stream phases.

The temperature control of the fluid mixer can—in addition to the geometric design—be of great importance with regard to the accuracy of the method. The temperature and the molecular properties have a considerable influence on the diffusion behavior of the substances. A fluid mixer used for gaseous fluids differs from a fluid mixer for liquid fluids, since the diffusion properties of liquids and gases differ.

The "fluid stream" passed through the supply element has a discontinuous composition when the composition of the volume flow is considered at a fixed point of the supply at consecutive points in time.

Regarding the term "concentration profile", it should be noted that this relates to one or more components. When considering the concentration of a single component A within the fluid stream in a particular volume element at a defined point of the fluid stream duct, the concentration of component A in this volume element can change with time. Consequently, plotting concentration against time gives the concentration profile.

The fluid stream comprises at least one component or a plurality of components and a carrier fluid stream also needs to be present if the fluid stream comprises only a single component. The fluid stream is generally a multicomponent system. In particular, the multicomponent systems to be investigated can also have a very complex structure.

It is apparent from the description of the composition of the fluid streams that the component or multiplicity of components may be present in very different concentrations. Furthermore, the concentration of the individual components can also change over time to a greater or lesser extent which is associated, for example, with the process by which the fluid stream is formed.

The method according to the invention is based on discontinuous fluid streams being generated. Defined (or discrete) regions of these fluid streams are selected and then integrally converted into a continuous region of a fluid stream in the fluid mixer (33). The continuous region is discharged via the outlet and parts of the fluid stream are supplied to an analytical process [(43) or (43/1), (43/2)].

In connection with the method according to the invention, it is possible, in the best case, to effect complete back-mixing of the fluid stream phase. This forms a commixed fluid stream phase having a constant or virtually constant concentration profile over a defined time range. The indication regarding the constant or virtually constant concentration profile relates to a commixed fluid stream in a conduit element downstream of the fluid mixer or in the fluid mixing space (33).

This means that a fluid stream phase having a discontinuous concentration profile is back-mixed inside the supply element (36) in the gas mixing space (33) or fluid mixing space (33) such that a mixture is formed which, over the back-mixing time constant, has a constant concentration of all comprising components and a concentration integral corresponding over time to the concentration integral over the duration of the fluid stream phase prior to the back-mixing of the fluid stream.

Quantifying the concentration of the back-mixed fluid stream at any point in time allows the integral amount of the fluid components of the cycle to be determined. Thus, the method according to the invention permits (parallelized) integral quantifying of components of a fluid stream having a discontinuous concentration profile.

The duration of the reactant stream phase is selected such that at least a significant part of the duration of the deactivation of the catalyst takes place in this duration. With regard to the catalytic process, this means that the decrease in activity of the process is in the range from 0.1% to 95% per second, preferably in the range from 1% to 50% per second.

In a preferred embodiment, the method according to the invention relates to the (analytical) characterization of fluid streams, wherein the fluid stream or fluid streams originate from a catalyst test apparatus for investigating catalytic processes and a gaseous fluid stream is concerned, wherein the GHSV is in the range of 250-200 000 $h^{-1}$, preferably of 500-150 000 $h^{-1}$ and more preferably of 500-100 000 $h^{-1}$.

The combination of substream withdrawal with downstream back-mixing is also an essential feature of the present invention. Substream withdrawal has the advantage that, particularly in the high GHSV range wherein GHSV values of 500 $h^{-1}$ are exceeded, the amount of product fluid stream is very high and exceeds the capacity of fluid mixing spaces (33/x) or the dimensions of the fluid mixing spaces (33/x) become unsuitably large for laboratory investigations, which is disadvantageous particularly for the parallelized arrangement of reaction spaces (21/x). The stated GHSV value of 500 $h^{-1}$ relates in the present case to catalyst volumes in the region of 1 mL.

The back-mixing is undertaken under precisely controlled conditions and the discontinuous product fluid stream can consequently be treated in a targeted and very well defined manner. It should be borne in mind that it can also be advantageous to employ a flushing step in the method in order to fill the gas mixer (33) (or the gas mixers (33/x)) with fluid stream having a similar composition to the fluid stream of the experimental investigation. When a flushing step is employed, the dead volume should be flushed through three times with this flushing fluid stream. With regard to the dead volume downstream of the reaction spaces (211x), the volume of the gas mixing space (33) has the largest volume and is only flushed through by the substream. Consequently the volume inside the gas mixing space (33) in particular should be replaced three times.

Consequently, in an advantageous embodiment, the method according to the invention also comprises a flushing step (i.x) upstream of step (i), said flushing step consisting of passing a suitable fluid through the supply line (36) to the gas mixing space including gas mixing space (33), wherein the volume of the fluid substream fills about three times the dead volume of this region of the apparatus.

However, the flushing step is not necessary when the method is carried out with the FIG. 2 shown in FIG. 2, wherein the gas mixing space (33) is disconnected from the supply of the fluid stream and the commixing of the fluid stream proceeds in part during the period in which no supply of fluid stream to the gas mixing space (33) is effected.

The method according to the invention is suitable for investigating all discontinuous processes in which discontinuous fluid streams arise. This may be the case, for example, in processes carried out in connection with temperature changes of the catalyst temperature or in processes carried out with feed changes (flow changes, concentration changes) or pressure changes. Furthermore, also in processes in connection with rapid catalyst deactivation (aging). The changes of the parameters referred to here can occur individually or together. The method is suitable for investigating reversible processes in particular.

Furthermore, in a preferred embodiment, the method for characterizing fluid streams comprises carrying out the method at a pressure in the range of 0.5-200 bar, preferably of 0.5-150 bar and more preferably of 0.5-100 bar.

The analysis times of the respective product fluid stream are also an influencing parameter with respect to the control and the course of the method. The analysis times depend both on the analyzer ((43) or (43/1), (43/2) respectively) employed in each case and on the complexity of the product mixture to be analyzed. Furthermore, the number of reaction spaces (21/x) installed in an apparatus is also important, namely whether, for example, four, eight, sixteen or more reaction spaces are arranged in parallel. The greater number of reaction spaces is connected to a greater number of gas mixing spaces (33/x). In this connection it is also evident that the construction of the apparatus is associated with greater technical demands concerning control and handling with an increasing number of reaction spaces (21/x) and of gas mixing spaces (33/x). An upper limit is therefore also set concerning the number of reaction spaces and gas mixing spaces. Given current levels of manufacturing performance and reaction spaces having an internal volume larger than 10 ml, it is preferable for the apparatus according to the invention to comprise fewer than 200 reaction spaces, preferably fewer than 100 reaction spaces and yet more preferably fewer than 50 reaction spaces. The indications mentioned here with regard to the upper limit for the number of reaction spaces (21/x) is not intended to limit the invention in any way.

It is preferable when every reactor is connected to one gas mixing space (33/x) each. It is also conceivable for a single reactor to be connected to two or more gas mixing spaces [(33/x'), (33/x'') . . . ] which can then be serially connected and filled in order to form product fluid subamounts here and undertake yet further kinetic investigations.

Account should be taken of the particular analysis time for the analysis of a product fluid stream collected in a gas mixing space (33) and the number of gas mixing spaces and also the number of analyzers (43/x) used for characterizing the product mixture from the gas mixing space. The analysis times are generally in the time range between 30 s and 1800 s. For example, the analysis time of a complex product mixture can be 1200 s. With regard to an apparatus comprising sixteen reactors arranged in parallel, an analysis time, for example, in the range from 4 to 6 hours can result in order to analyze all product mixtures in the sixteen gas mixing spaces. The example given here relates to an apparatus which is provided with an analyzer and in which every reactor is connected to one gas mixing space each.

EXAMPLES

To illustrate the method according to the invention, several illustrative investigations were carried out with a catalyst test apparatus which was provided with different gas mixing vessels on its reaction space outlet side prior to the particular investigation. The examples set out here are not intended to limit the invention in any way. The molar concentration of fluid component 1 (i.e. in the present case ethane) was characterized using a GC (namely an Agilent 7890A, TCD column: CP-Volamin 30 m×0.32 mm×5 µm, run time 4.6 min (7.2 min from start to start)). The results of these investigations are shown in tables 1 to 3. The gas mixing vessels were heated and the temperature of the gas mixing vessels was 50° C. in each case. The experimental parameters were selected such that the pressure in the reaction space was 0.17 barg (i.e. 1.17 bar) in each case.

Table 1 shows the results of a first series of investigations wherein the duration of the fluid phases introduced into the gas mixing vessel was varied. Ethane was used as fluid phase 1 (with a flow rate of 83.3 mL/min) and nitrogen was used as fluid phase 2 (with a flow rate of 62.6 mL/min) and these were alternatingly introduced into the gas mixing vessel. [The same flow rates—i.e. 83.3 mL/min of ethane stream and 62.6 mL/min of $N_2$ stream—were also used in examples E5-E8. The indications given here refer to standard liters.] Consequently, a single cycle consisted of a phase 1 in which ethane was introduced into the gas mixing vessel and a phase 2 in which nitrogen was introduced into the gas mixing vessel. Identical phase durations were selected for phase 1 and phase 2 in all examples. The duration of the fluid phases were 5 minutes in each case in example 1, 10 minutes in each case in example 2 and 20 minutes in each case in example 3. This resulted in a cycle duration of 10 minutes for example 1, of 20 minutes for example 2, and of 40 minutes for example 3. The switching times between the different phases and cycles were in the region of milliseconds and consequently had no bearing on the investigation. The ethane concentration was determined and the percentage standard deviation (STDP) calculated in order to demonstrate the accuracy of the method. Comparison with analysis of a 50.5% by volume ethane stream in example E4 gives a percentage standard deviation of 0.15% and demonstrates the performance and the efficiency high accuracy for the experimental examples according to the method of the invention. The following formula was used as a basis for calculating the standard deviation:

$$STDP=[SQRT[\Sigma(Xt-Xm)^2/n]/Xm]*100.$$

Here, Xi is the measured value in question, Xm is the mean value and n is the number of measurements.

The duration of a cycle is made up of the duration of the individual phases, i.e. in the present case $T_{cycle}=T_{P1}+T_{P2}$.

In the experiments shown in tables 2 and 3, the phase durations were selected such that every individual phase had a duration of 5 minutes. This resulted in a cycle time of 10 minutes. The cycles were repeated at least ten times in the space of one experiment. The ratio of the retention time $t_{rt}$ to the cycle duration $T_{cycle}$ is a characteristic parameter for the method according to the invention. The ratio of retention time to cycle duration ($t_{rt}/T_{cycle}$ ratio) should have a value greater than 4. In this connection it should be noted that a conclusive indication of a preferred value of this parameter can be given here only with difficulty. It is conceivable that improvements to the equipment available—for example the use of improved fluid mixers—could lead to a change in the value of the $t_{rt}/T_{cycle}$ ratio compared to what is indicated here.

In examples E1 to E8, an experimental duration of 1.5 hours each was selected, wherein in each case 15 analyses were undertaken during this duration. The vessels were flushed for 6.4 hours beforehand in order to achieve adjustment of the new mixture. A throttle element operated with a pressure difference of 0.17 bar was used. The substream passed through the throttle had a volume flow of about 1 mL/min with. Since the withdrawal of sidestream withdraws a constant flow from the reactor output stream, the back-mixed concentration corresponds to the time proportions of ethane and nitrogen.

A plot of the measured results in FIGS. 9 and 10 shows that the quantitative measurements of the ethane content show slight differences attributable to very small pressure variations of the apparatus. Divergences of this type in the quantitative indication of the measurements can be compensated by means of addition of internal standard. These pressure variations arise on fluid change. Their contribution is therefore proportional to the frequency of the fluid changes ($\sim 1/T_{cycle}$). Independent of the divergence of the absolute values, the variation in the measurements is within the range of accuracy of the analyzer and this consequently demonstrates the particular usefulness of the method according to the invention.

Table 1 shows a representation of the experimental parameters and test results of a back-mixing experiment using a setup and method according to the invention, wherein in examples E1 to E3 the length of the phase duration was altered. A fluid mixing space formed from three sequentially arranged vessels was used in all three examples. Each individual vessel had an internal volume of 50 mL, therefore giving a total internal volume of 150 mL in this case. For comparison, in E4 a similar ethane concentration was determined with the same analysis unit. E4 therefore illustrates the accuracy of the analysis.

| Ex. | Vol. of gas mixing vessel [mL] | $t_{rt}/T_{cycle}$ [min/min] | Temp. of gas mixing vessel [° C.] | $T_{P1}$ (ethane) [min] | $T_{P2}$ (nitrogen) [min] | STDP of ethane analysis [%] |
|---|---|---|---|---|---|---|
| E1 | 3 × 50 | 15 | 50 | 5 | 5 | 0.24 |
| E2 | 3 × 50 | 7.5 | 50 | 10 | 10 | 0.18 |
| E3 | 3 × 50 | 3.75 | 50 | 20 | 20 | 0.47 |
| E4 | — | — | | | | 0.15 |

Table 2 shows a representation of the experimental parameters and test results of a back-mixing experiment using a setup and method according to the invention, wherein the influence of the geometry of the gas mixing vessel was investigated. In example E5, an arrangement of three sequentially arranged vessels was used. Every one of the three vessels had an internal volume of 50 mL. In example E6, a single gas mixing vessel having an internal volume of 150 mL was used.

| Ex. | Vol. of gas mixing vessel [mL] | $t_{rt}/T_{cycle}$ [min/min] | Temp. of gas mixing vessel [° C.] | $T_{P1}$ (ethane) [min] | $T_{P2}$ (nitrogen) [min] | STDP of ethane analysis [%] |
|---|---|---|---|---|---|---|
| E5 | 3 × 50 | 15 | 50 | 5 | 5 | 0.24 |
| E6 | 150 | 15 | 50 | 5 | 5 | 2.74 |

Table 3 shows a representation of the experimental parameters and test results of a back-mixing experiment using a setup and method according to the invention, wherein the effect of the internal volume of the gas mixing vessel on mixing efficiency was determined. In example E7 a gas mixing vessel having an internal volume of 75 mL was used and in example E8 a gas mixing vessel of 150 mL was used.

| Ex. | Vol. of gas mixing vessel [mL] | $t_{rt}/T_{cycle}$ [min/min] | Temp. of gas mixing vessel [° C.] | $T_{P1}$ (ethane) [min] | $T_{P2}$ (nitrogen) [min] | STDP of ethane analysis [%] |
|---|---|---|---|---|---|---|
| E7 | 75 ml | 7.5 | 50 | 5 | 5 | 3.32 |
| E8 | 150 ml | 15 | 50 | 5 | 5 | 2.74 |

To illustrate the apparatus according to the invention and the method according to the invention, further illustrative investigations were carried out with a parallelized catalyst test apparatus. This apparatus had, on the outlet side to the respective reaction space, a 50 mL fluid vessel which was heated to 200° C. Downstream of the fluid vessel was a substream withdrawal according to the invention, which was operatively connected to three 50 mL fluid mixing vessels arranged in series and heated to 200° C. For qualitative and quantitative analysis of the product composition, the two substreams of the product stream were each analyzed with one analytical instrument. The test reaction investigated was the conversion of propane in the presence of acidic catalysts in the temperature range of 500-600° C. Three different catalyst materials (see table 4) were investigated in various reactor charges (catalyst volumes) and various mixtures with inert material. In the case of the mixtures, a distinction was made between virtually homogeneous mixing of catalyst material and inert material (physical mixture) and a separate ("layered") mixture (see table 5). The investigation of the catalysts was effected by means of one embodiment of the test method according to the invention, in which each individual catalyst was subjected to a relatively large number of cycles, with each individual cycle composed of four phases. In a first phase, a propane-containing reactant stream was converted over the particular catalyst. The catalyst was regenerated in an oxygen-containing regeneration phase.

Between the reactant stream phase and regeneration phase in each case was an inert gas stream phase (nitrogen in the present case), in order to separate reactant stream atmosphere and regeneration stream atmosphere over the catalyst. For qualitative and quantitative analysis and for calculation of the change in the composition of the product stream over time, a substream was analyzed with an analytical instrument downstream of the fluid mixing spaces, passing through 29 cycles between two measurement points at one temperature. Within the same period, in the second substream which was not directed through the fluid mixing space, the product stream composition was analyzed continuously with a second analytical instrument. On the basis of the data obtained here, the integral product stream composition was determined over a multitude of cycles and correlated with the corresponding reactant stream. In accordance with this description, the product stream analysis was conducted for each change in the reaction conditions (temperature or duration of a reactant stream phase) from the juncture from which the product stream phase does not have any variation with time as a result of back-mixing effects from the fluid mixing spaces. To determine the necessary duration, preliminary experiments were conducted analogously to the investigation described in FIG. 9. For the quantitative statement of product stream compositions, to improve clarity, the hydrocarbons having a number of six or more carbon atoms were combined of the compound group having six carbon atoms (i.e. carbon number 6). To further improve clarity, high molecular weight carbon compounds (i.e. coke in the present case) which have been deposited on the catalyst in the reactant stream phase and removed from the catalyst in the regeneration phase have been combined in the product stream composition of the compound group having one carbon atom (i.e. carbon number 1).

Table 4 shows the material properties of the catalysts used in these experiments.

| Sample designation | Manufacturer | $SiO_2/Al_2O_3$ | Surface area [m$^2$/g] |
|---|---|---|---|
| CBV 3024E | Zeolyst | 30 | 405 |
| CBV 8014 | Zeolyst | 80 | 425 |
| CBV 28014 | Zeolyst | 280 | 400 |

Table 5 shows the amount of catalyst and inert material used in these experiments and the manner of arrangement of these materials in the reactor. The inert material served as diluent.

| Catalyst example | Catalyst | m(catalyst) (particle size 100-120 μm) [g] | m(inert material) (particle size 100-120 μm) [g] | Manner of arrangement in the reactor (type of catalyst/inert material mixture) |
|---|---|---|---|---|
| K1 | CBV 3024E | 0.291 | 0 | — |
| K2 | CBV 3024E | 0.097 | 0.644 | separately (i.e. inert beneath the catalyst) |

-continued

| Catalyst example | Catalyst | m(catalyst) (particle size 100-120 μm) [g] | m(inert material) (particle size 100-120 μm) [g] | Manner of arrangement in the reactor (type of catalyst/inert material mixture) |
|---|---|---|---|---|
| K3 | CBV 3024E | 0.193 | 0.323 | separately (i.e. inert beneath the catalyst) |
| K4 | CBV 3024E | 0.098 | 0.644 | physical mixture |
| K5 | CBV 3024E | 0.193 | 0.323 | physical mixture |
| K6 | CBV 8014 | 0.275 | 0 | — |
| K7 | CBV 8014 | 0.093 | 0.644 | separately (i.e. inert beneath the catalyst) |
| K8 | CBV 8014 | 0.183 | 0.323 | separately or stacked arrangement |
| K9 | CBV 8014 | 0.093 | 0.644 | physical mixture |
| K10 | CBV 8014 | 0.183 | 0.322 | physical mixture |
| K11 | CBV 28014 | 0.301 | 0 | — |
| K12 | CBV 28014 | 0.101 | 0.643 | separately (i.e. inert beneath the catalyst) |
| K13 | CBV 28014 | 0.200 | 0.322 | separately (i.e. inert beneath the catalyst) |
| K14 | CBV 28014 | 0.100 | 0.644 | physical mixture |
| K15 | CBV 28014 | 0.201 | 0.322 | physical mixture |

Table 6 shows the analysis system used for these experiments for quantitative determination of the fluid components of the product stream.

| Analytical instrument 1 | |
|---|---|
| Gas chromatograph | Agilent 7890A |
| Column | Volamin, Rtx1, PlotQ, Carboxen, molecular sieve |
| Carrier gas | argon, hydrogen, helium |
| Duration of an analysis (start to start) | 45 min (i.e. about one measurement every 45 min) |
| Detectors | Flame ionization detector, thermal conductivity detector, methanizer |
| Analytical instrument 2 | |
| IR analyzer | ABB AO2000 system |
| CO measurement range | 0-5 vol % |
| CO2 measurement range | 0-10 vol % |
| Measurement frequency | 1 measurement per second |

Table 7 shows the reaction parameters used for these experiments, which were used for the testing of the catalysts listed in table 4.

| Reactant stream phase | |
|---|---|
| Duration | 10 s or 20 s |
| Composition | 20 vol. % of propane + 80 vol. % of argon |
| Flow rate | 1333 mL/min |
| Inert gas stream phase | |
| Duration | 120 s |
| Composition | nitrogen |
| Flow rate | 1333 mL/min |
| Regeneration phase | |
| Duration | 1200 s |
| Composition | air |
| Flow rate | 1333 mL/min |
| Inert gas stream phase | |
| Duration | 120 s |
| Composition | nitrogen |
| Flow rate | 1333 mL/min |
| Number of cycles between measurement points at a temperature | 29 |
| Reactor temperature | 500-600° C. |
| Pressure | 1 barg |
| Temperature of the fluid mixing vessels | 220° C. |
| Reactor volume | 0.5 mL |

FIG. 12 shows the propane conversions of the three undiluted catalysts K1, K6 and K11 at 500° C., 550° C. and 600° C. It is apparent here that a distinctly higher conversion was achieved with rising temperature, K1 being much more active at every temperature than example K6 and example K11. At a temperature of 550° C., a decrease in the activity over time was observed for K1 and K6. The decrease in activity over time was likewise observed at a temperature of 600° C. Lengthening the reactant stream phase from 10 s to 20 s at a temperature of 550° C. did not lead to a significant change in the deactivation rate. The activity and decrease in activity over time correlate with the material properties listed in table 4.

FIG. 13, FIG. 15 and FIG. 17 show the influence of the amount of catalyst and the influence of the GHSV on the activity using the example of the respective catalyst material. It is apparent that a higher conversion is achieved with increasing amount of catalyst. The deactivation rate is similar for all amounts of catalyst at the particular temperature.

FIG. 14, FIG. 16 and FIG. 18 show the influence of catalyst dilution and hence indirectly the influence of heat of reaction on the activity of the catalyst at the particular temperatures. It is apparent that undiluted catalysts tend to achieve a higher propane conversion.

In FIG. 12 to FIG. 18, changes in the reaction parameters (temperature or duration of the reactant stream phase) are emphasized by vertical dashed lines. In detail, the reaction conditions specified apply from the time point marked to the next marking or to the end of the experiment shown in the figure.

FIG. 19 shows the product distribution of K1, which was determined in each case at the first measurement point for the individual temperature stages, i.e. at 500° C., 550° C. and 600° C. It is apparent that the C3 yield and especially the propane yield became lower with rising temperature, whereas the C1, C2(paraffin), C2(olefin), C3(olefin) and C6 yields rise with rising temperature. Similar trends were likewise observed for K6 (FIG. 20) and for K11 (FIG. 21), the differences in the product distribution correlating with the lower activity of the respective catalyst.

FIG. 22 shows the product distribution of each measurement point for K1 at 500° C. Because there is barely any change in propane conversion over time (cf. FIG. 12) at this temperature, the product stream composition can be used as an indicator of the reproducibility of the measurement.

FIG. 23 shows the product distribution of each measurement point (at different times) for K1 at 600° C. It is apparent that, as can already be seen from FIG. 12, the propane yield rises over time and the propane conversion falls over time. Furthermore, it can be seen that the C6 yield falls with time at a temperature of 600° C.

BRIEF DESCRIPTION OF THE FIGURES

FIG. 8.a shows a schematic diagram of the influence of the gas mixing vessel according to the invention on a sequence of reactant fluid phases A (A1-A4) which is back-mixed by the arrangement according to the invention such that a concentration B can be determined using an analysis unit.

FIG. 8.b shows a schematic diagram of an apparatus based on the working example described in FIG. 6 but with the exception that no gas mixing vessel is used. C shows a non-stationary concentration profile.

Figure 1:
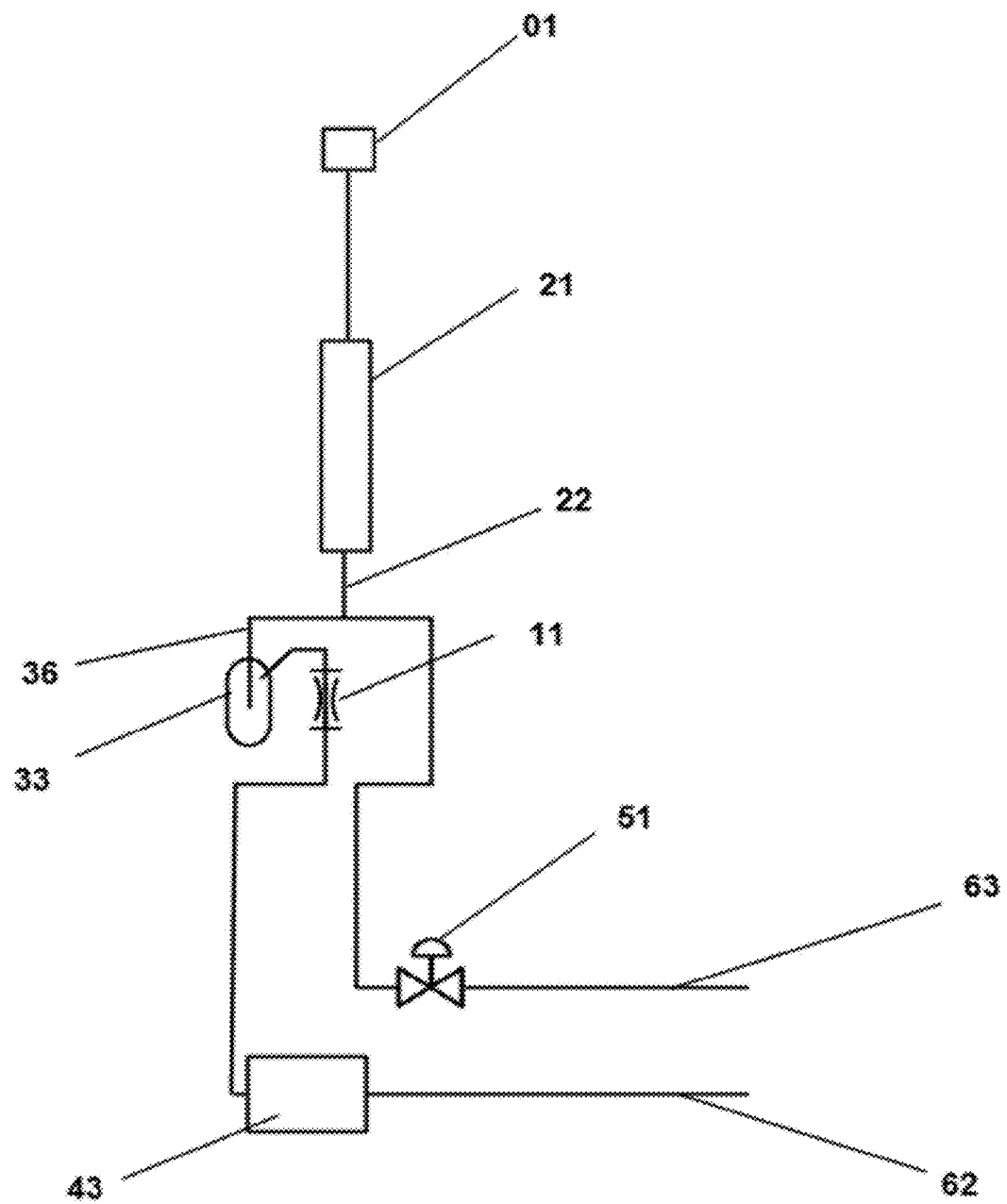
FIG. 1 shows a schematic diagram of the apparatus for investigating reactions in a cyclic mode of operation, wherein a reaction space (21) is operatively connected to a gas mixing space (33) via a substream line (36).
Figure 2:
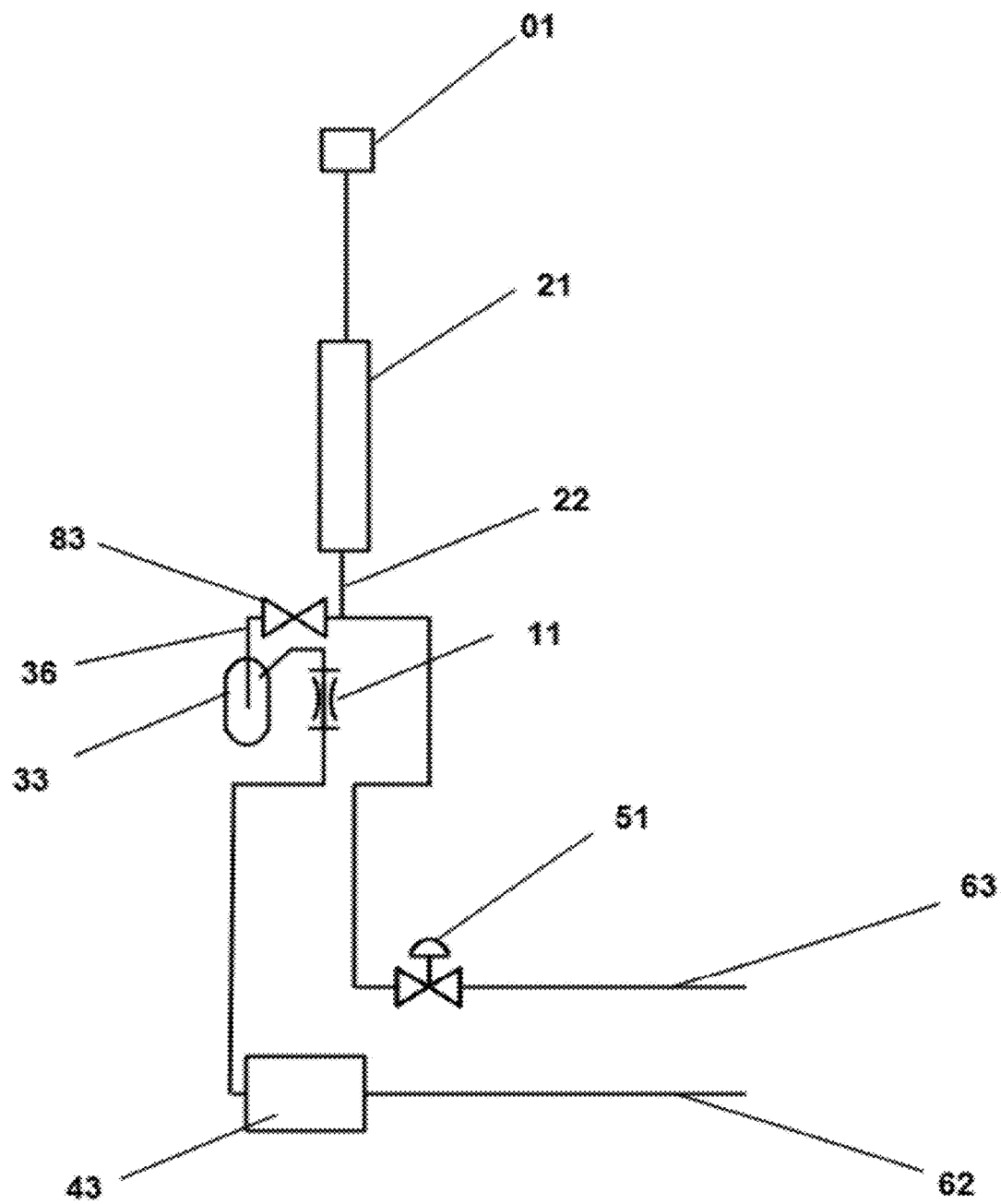
FIG. 2 shows a schematic diagram of the apparatus for investigating reactions which is identical to the apparatus shown in FIG. 1 with the exception that, on the inlet side of the fluid mixing vessel (33), a switching valve (83) is operatively connected to a fluid mixing vessel (33) via a substream line (36). Furthermore, a gas supply apparatus (02) is in interaction with the switching valve (83).
Figure 3:
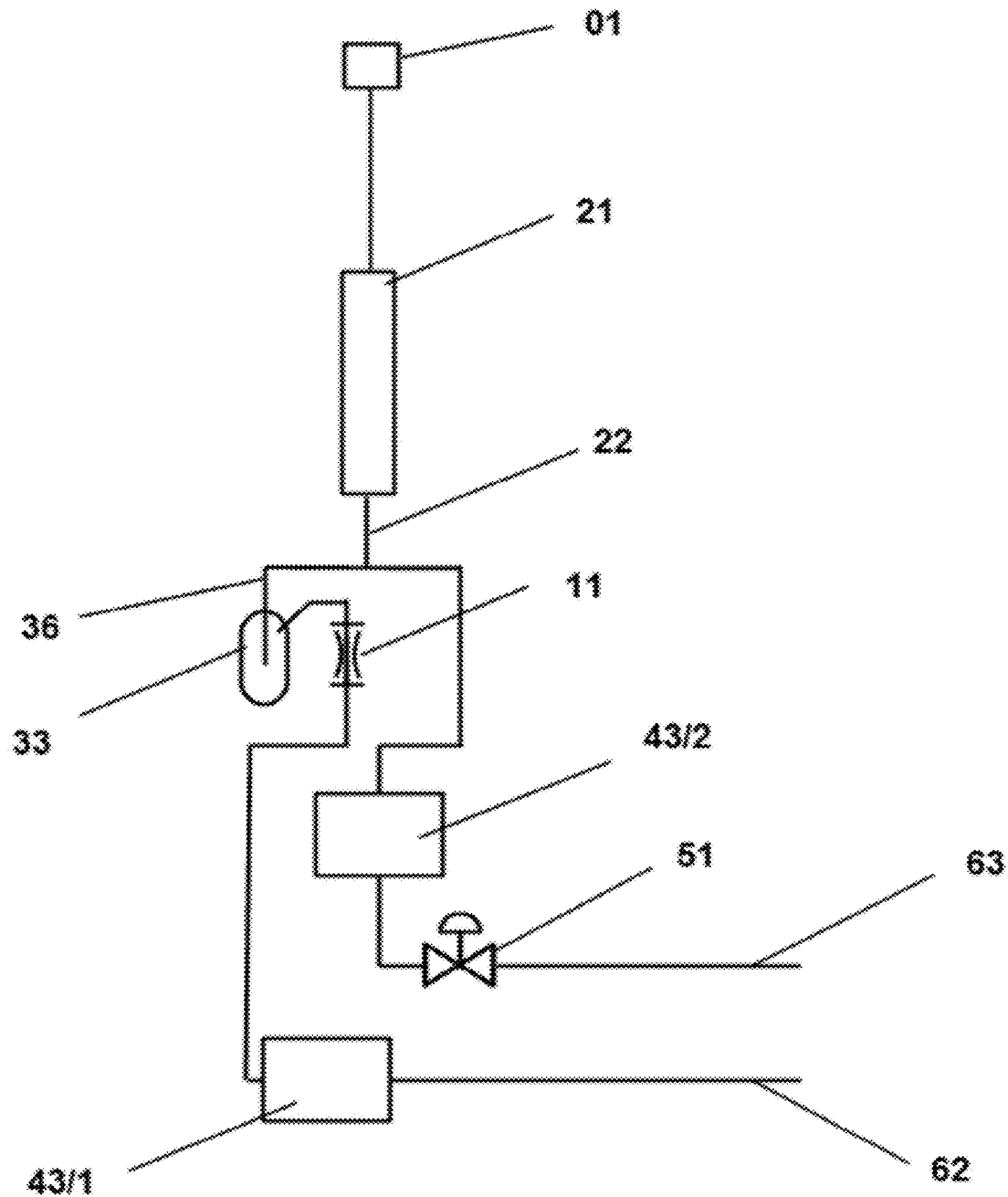
FIG. 3 shows a schematic diagram of the apparatus for investigating reactions in a cyclic mode of operation, wherein a reaction space (21) is operatively connected to a gas mixing space (33) via a substream line (36). Furthermore, an analysis unit (43/2) is located on the inlet side of the control valve (51).
Figure 4:
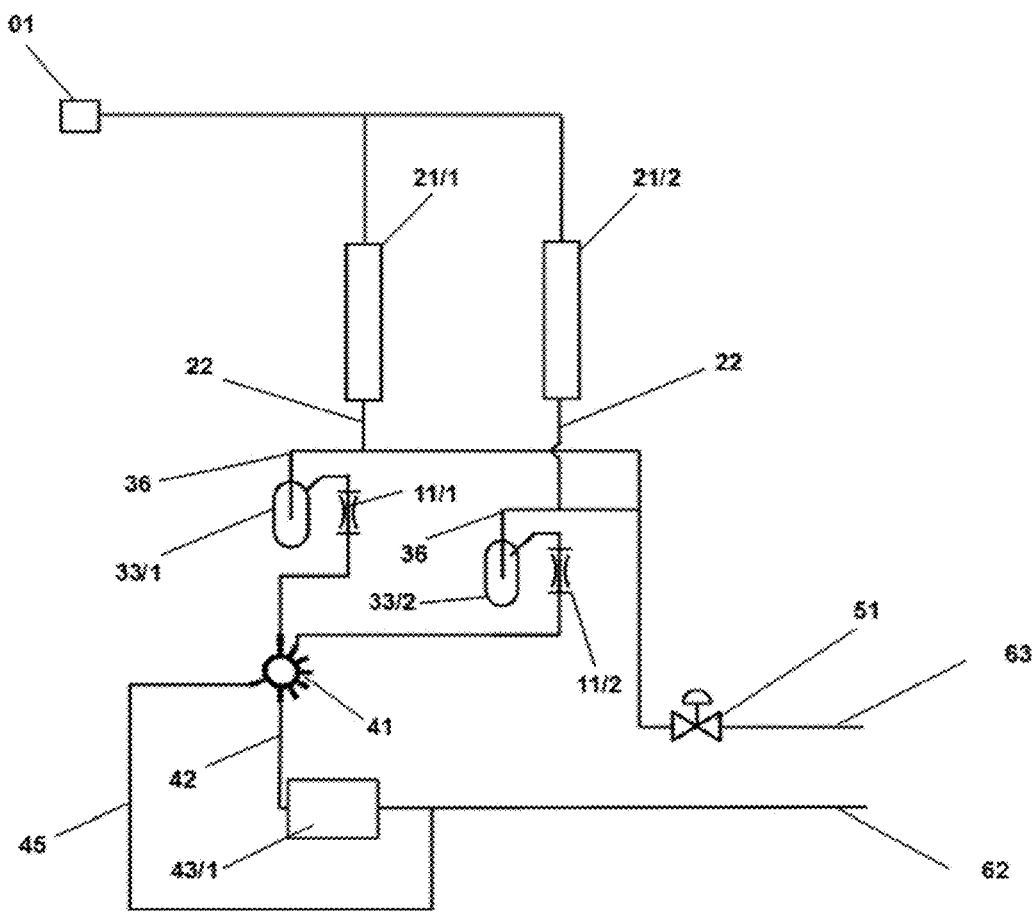
FIG. 4 shows a schematic diagram of an apparatus for investigating reactions, wherein the outlet side of every reactor space (21/1, 21/2) is operatively connected to a sidestream line (36) which, in turn, is connected to a gas mixing vessel (33/1, 33/2). The outlet side of every gas mixing vessel (33/1, 33/2) is operatively connected to the multiport valve (41) via a restrictor element (11/1, 11/2).
Figure 5:
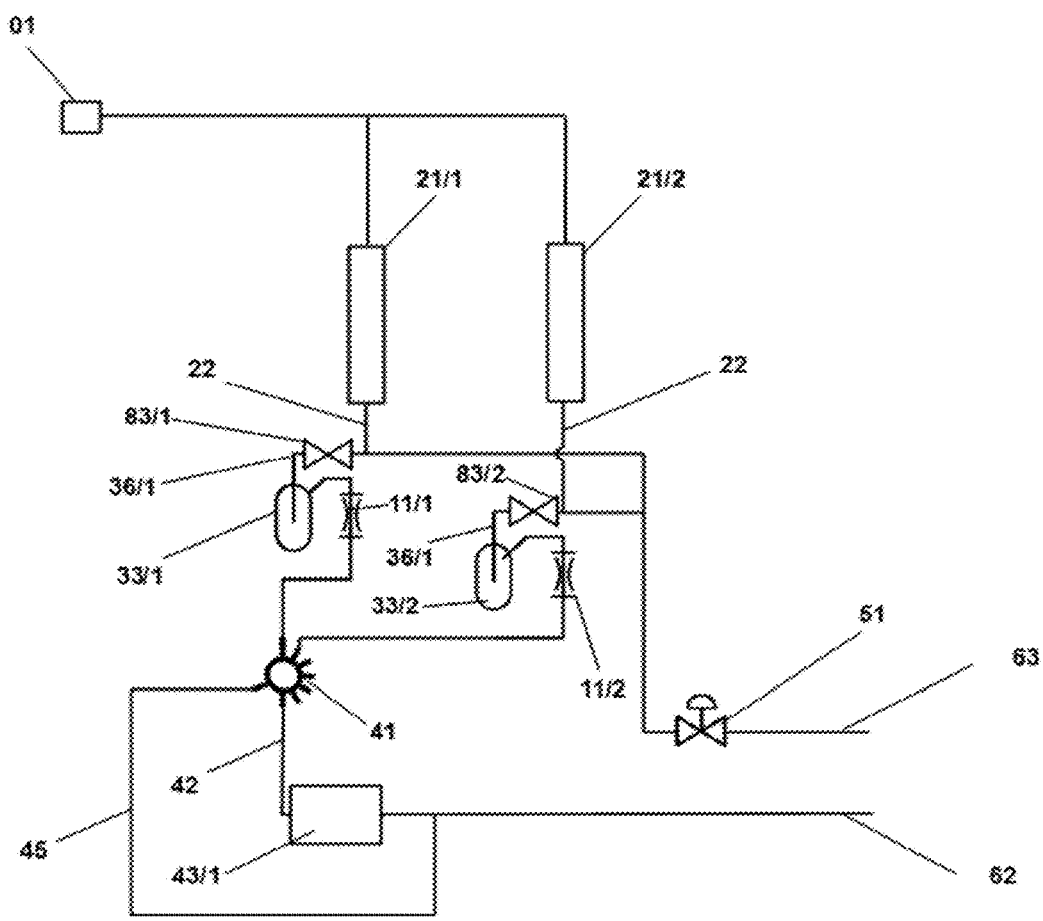
FIG. 5 shows a schematic diagram of an apparatus for investigating reactions which is identical to the apparatus shown in FIG. 4 with the exception that on the inlet side of every fluid mixing vessel (33/x), a switching valve (83/x) is operatively connected to a fluid mixing vessel (33/x) via a substream line (36/x). Furthermore, a gas supply apparatus (02/x) is in interaction with the switching valve (83/x).
Figure 6:
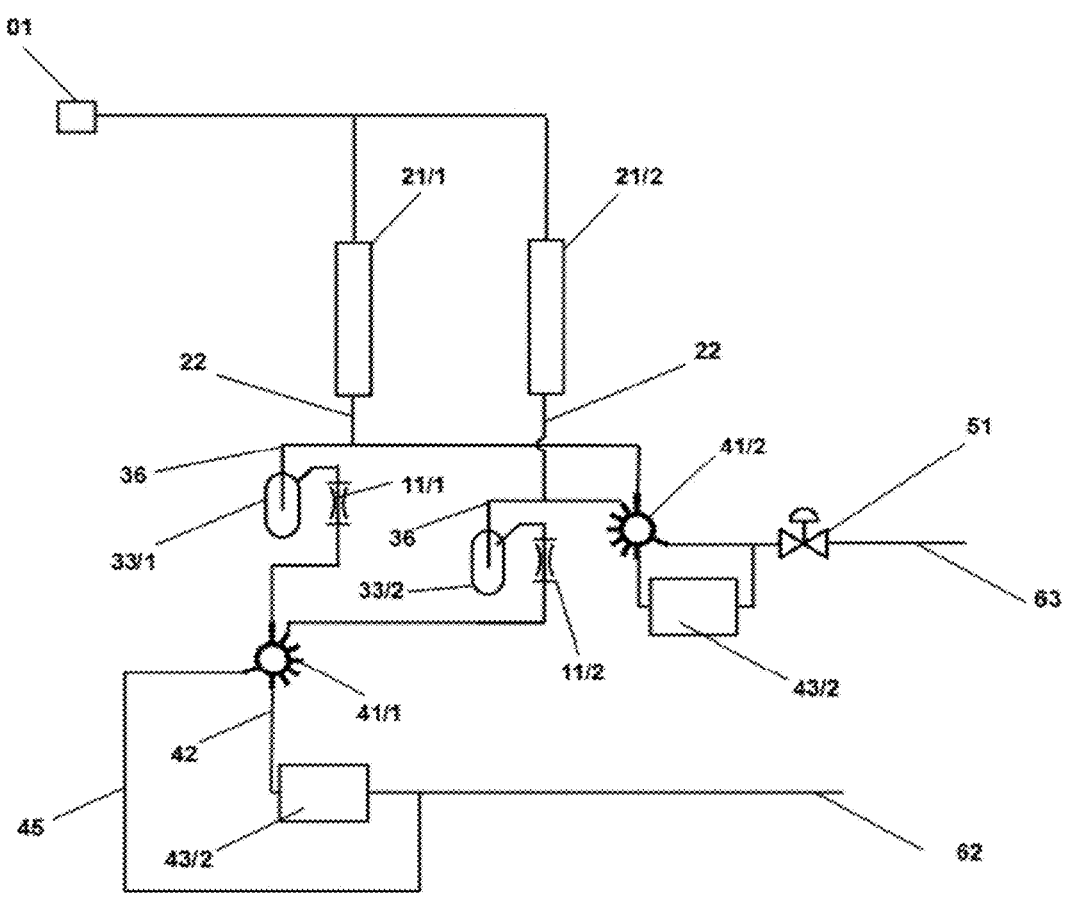
FIG. 6 shows a schematic diagram of an apparatus for investigating reactions which is identical to the apparatus shown in FIG. 4 with the exception that the connection on the reactor outlet side of an every reactor space (21/1, 21/2) is operatively connected to a multiport valve (41/2). There is an operative connection to the control valve (51) on the outlet side of the multiport valve (41/2).
Figure 7:
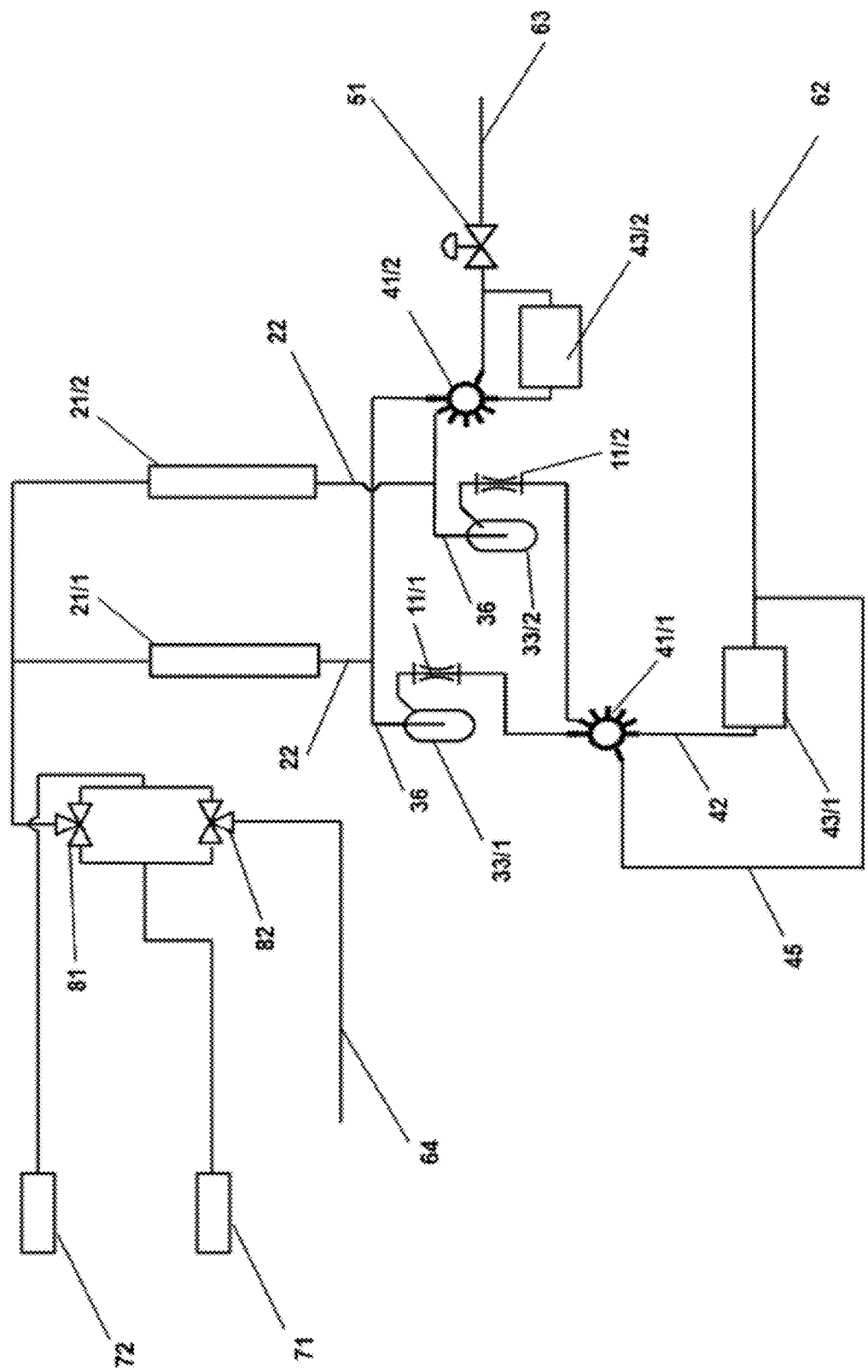
FIG. 7 shows a schematic diagram of an apparatus for investigating reactions which is identical to the apparatus shown in FIG. 4 with the exception that the fluid supply component consisting of valve 1 (81), valve 2 (82), gas supply apparatus for fluid component A and gas supply apparatus for fluid component A.
Figure 9:
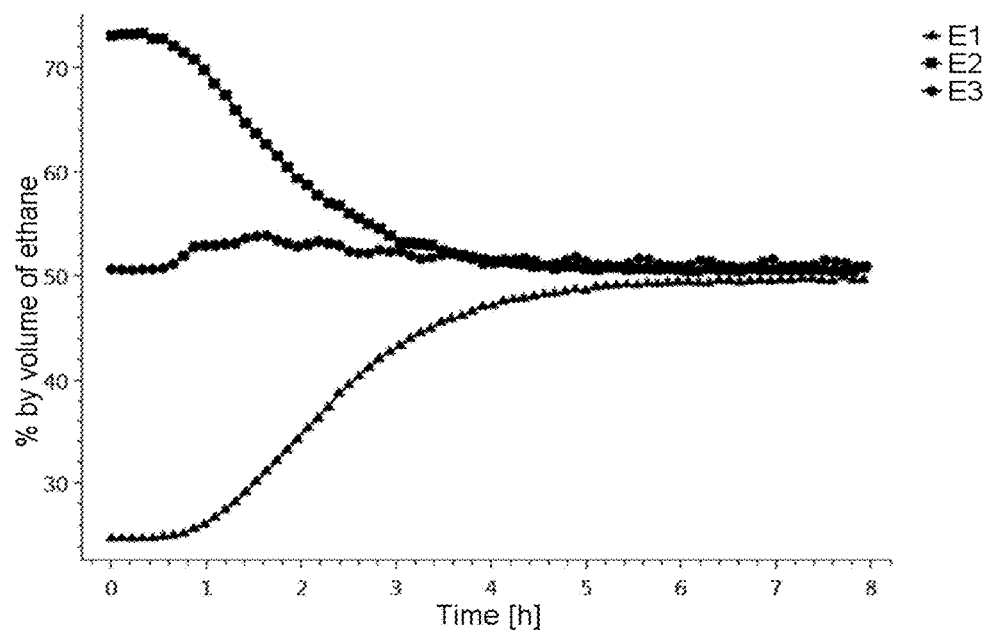
FIG. 9 shows the plot against time of the measured ethane concentrations including the flushing time for examples E1, E2, E3.
Figure 10:
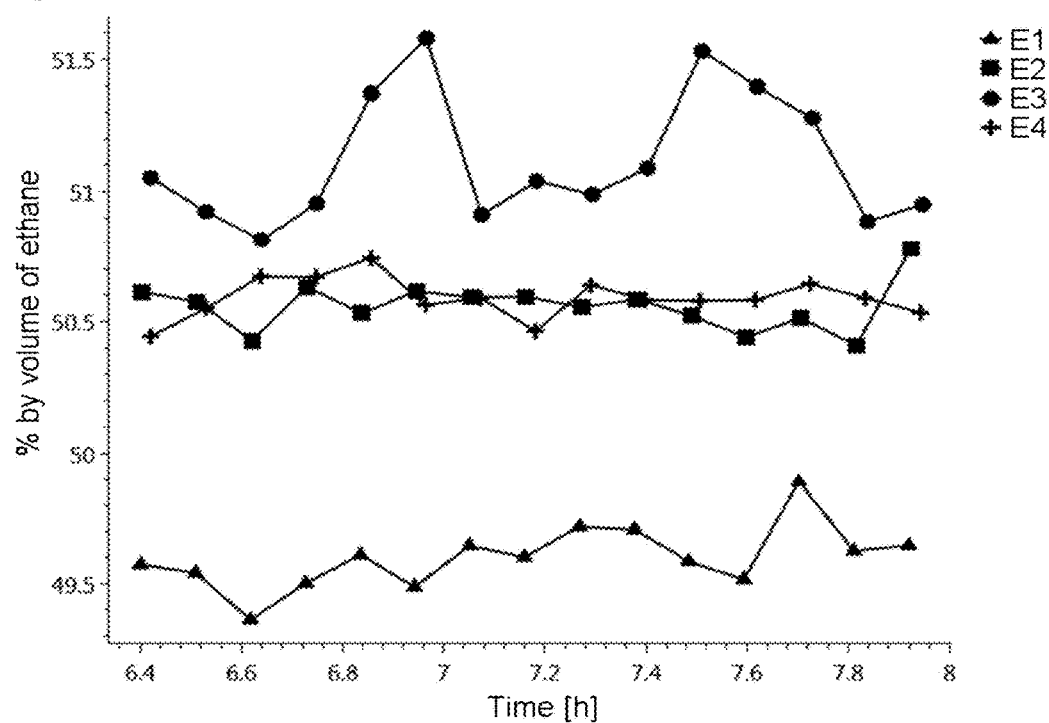
FIG. 10 shows the plot against time of the measured ethane concentrations after stabilization of the concentrations for the examples E1 to E4. The values were used for determining the percentage standard deviation. When the cycle time (E3) is too long, variation of the concentration with a period interval analogous to the cycle time can be discerned.
Figure 11:
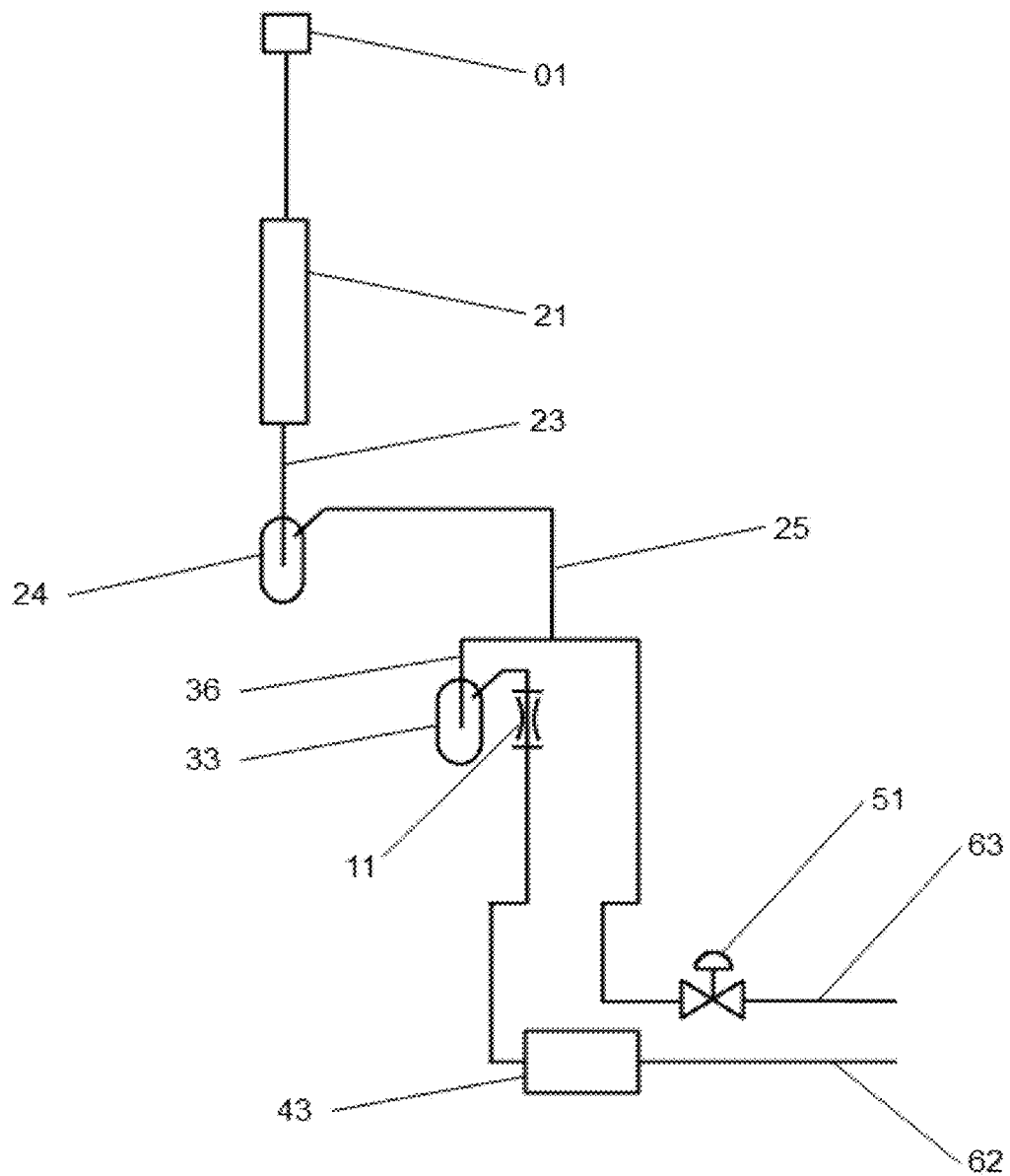
FIG. 11 shows a schematic diagram of the apparatus for investigating reactions which is identical to the apparatus shown in FIG. 1 with the exception that, on the outlet side of the reaction space (21), a fluid vessel (24) is operatively connected to the substream line (36).
Figure 12:
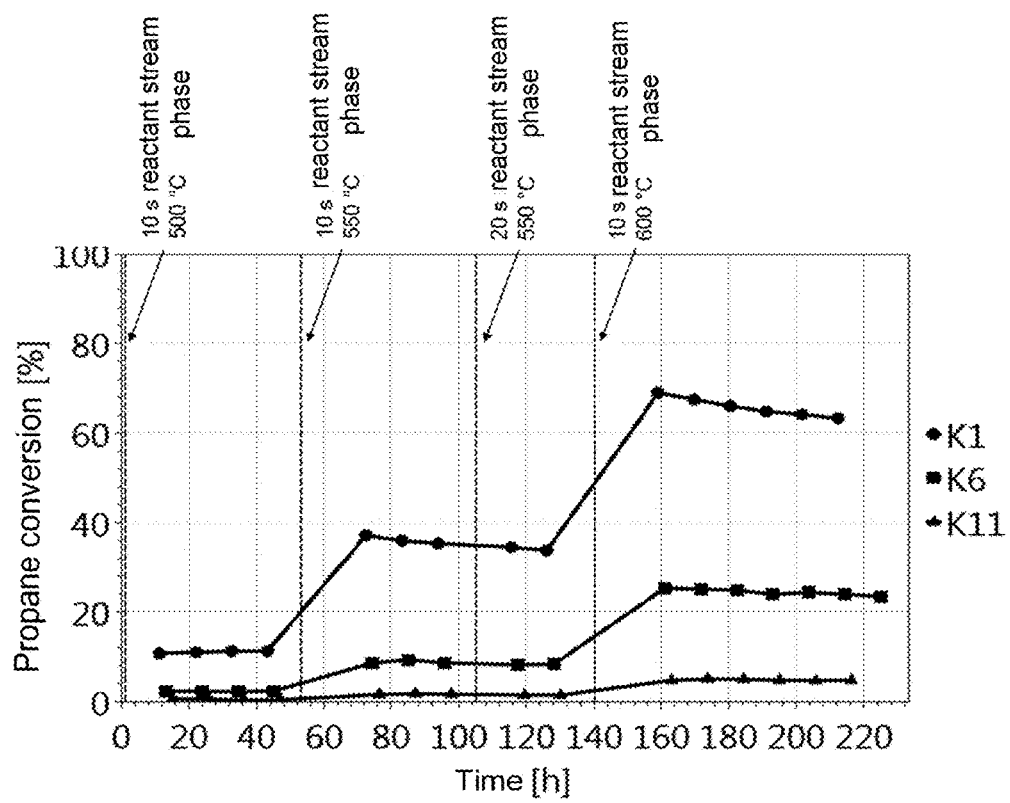
FIG. 12 shows the plot of the propane conversion for K1, K6 and K11 against time with the reaction parameters listed in table 7.
Figure 13:
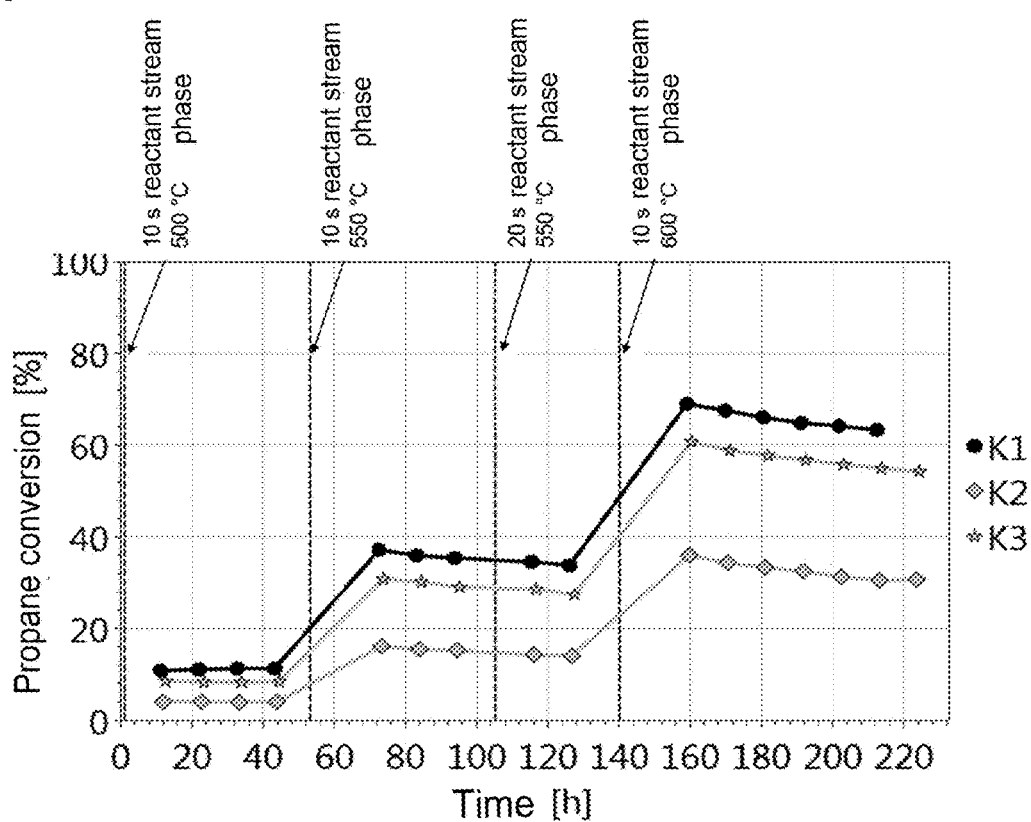
FIG. 13 shows the plot of the propane conversion for K1, K2 and K3 against time with the reaction parameters listed in table 7.
Figure 14:
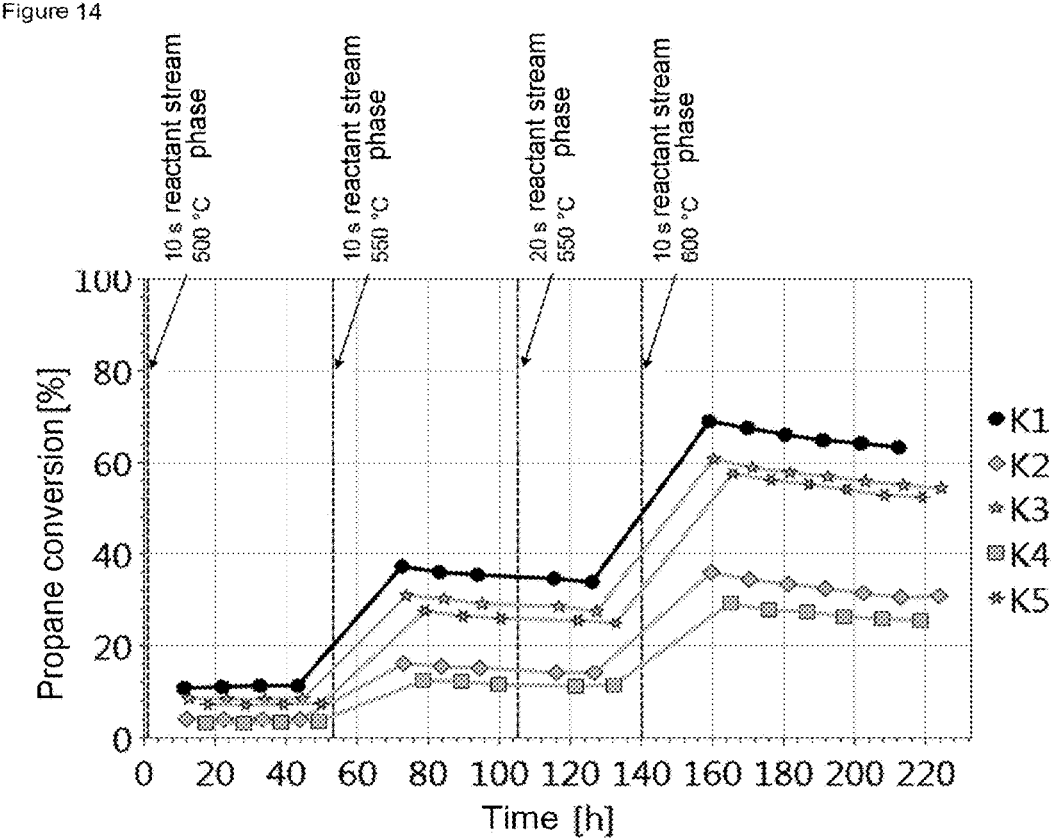
FIG. 14 shows the plot of the propane conversion for K1, K2, K3, K4 and K5 against time with the reaction parameters listed in table 7.
Figure 15:
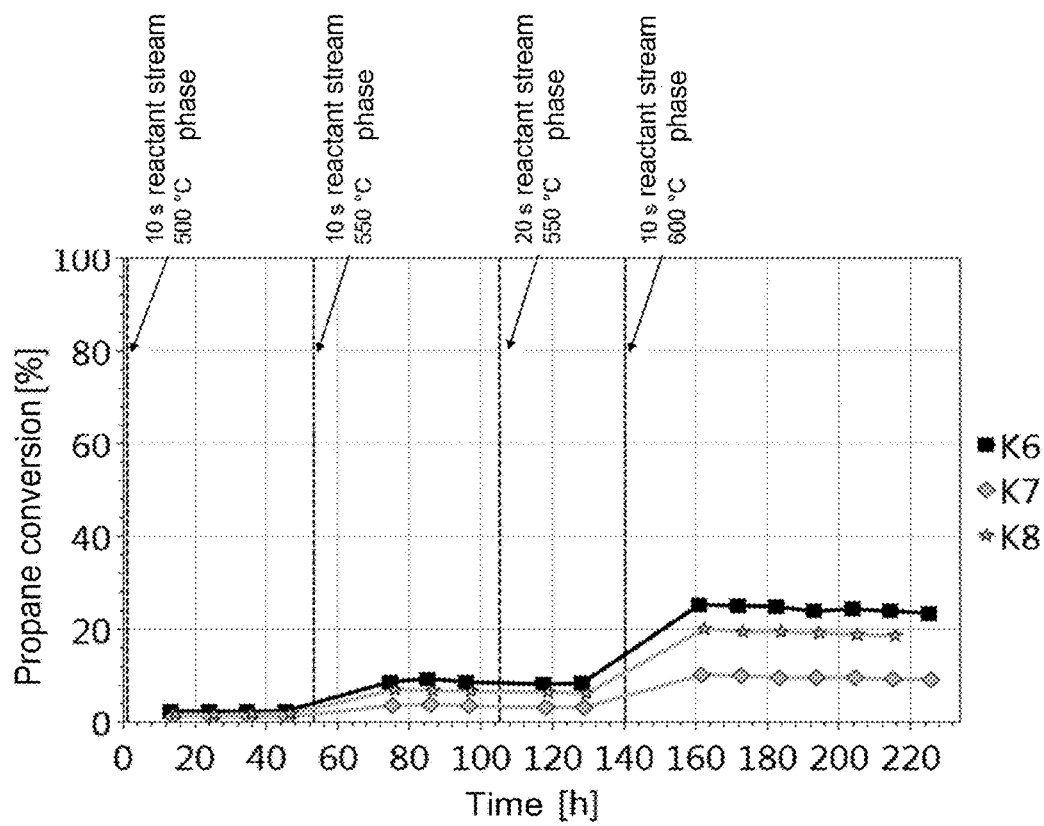
FIG. 15 shows the plot of the propane conversion for K6, K7 and K8 against time with the reaction parameters listed in table 7.
Figure 16:
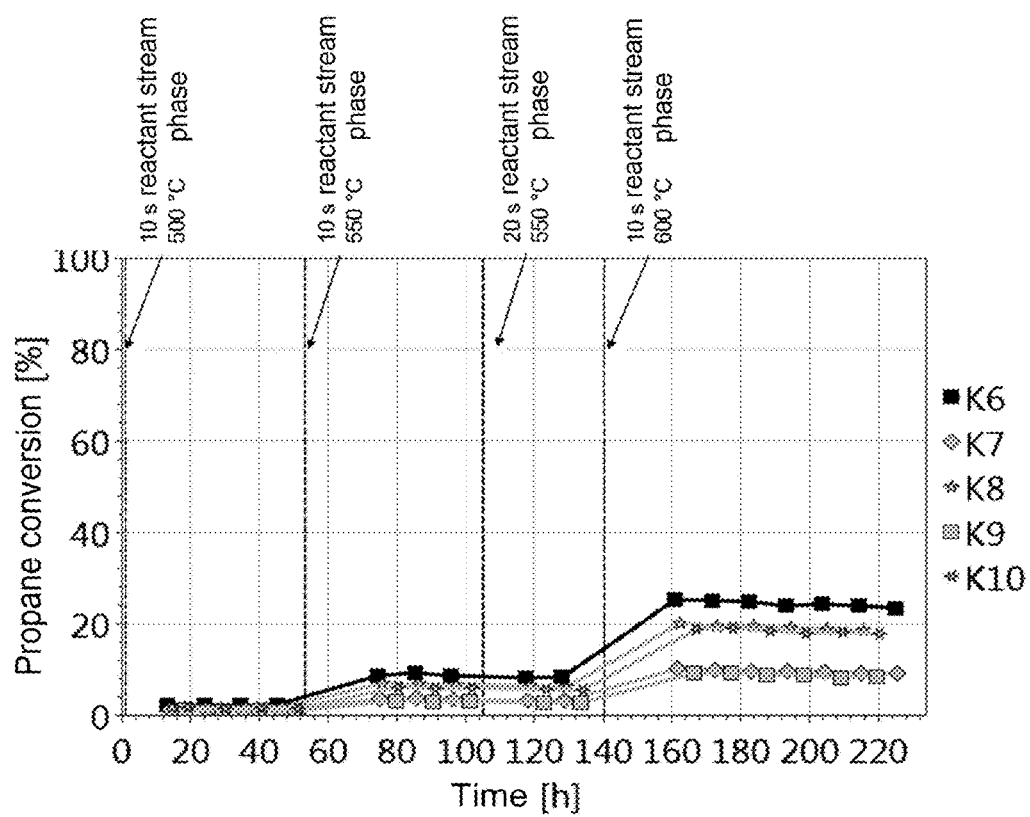
FIG. 16 shows the plot of the propane conversion for K6, K7, K8, K9 and K10 against time with the reaction parameters listed in table 7.
Figure 17:
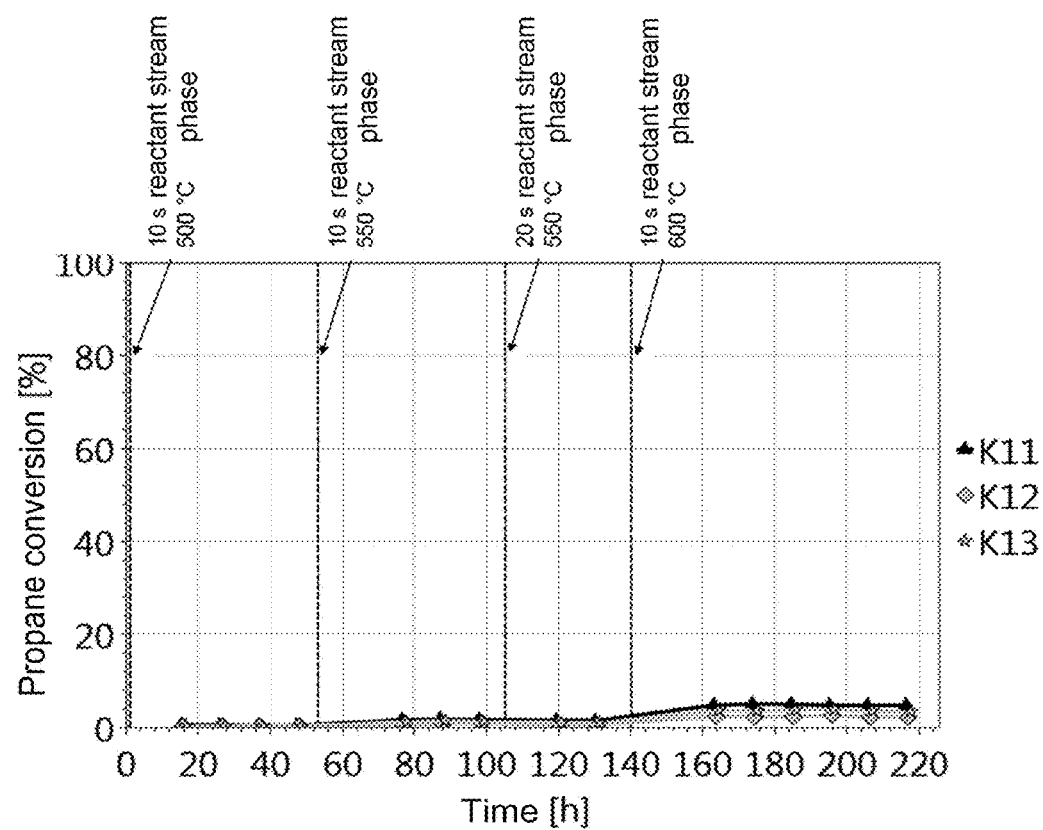
FIG. 17 shows the plot of the propane conversion for K11, K12 and K13 against time with the reaction parameters listed in table 7.
Figure 18:
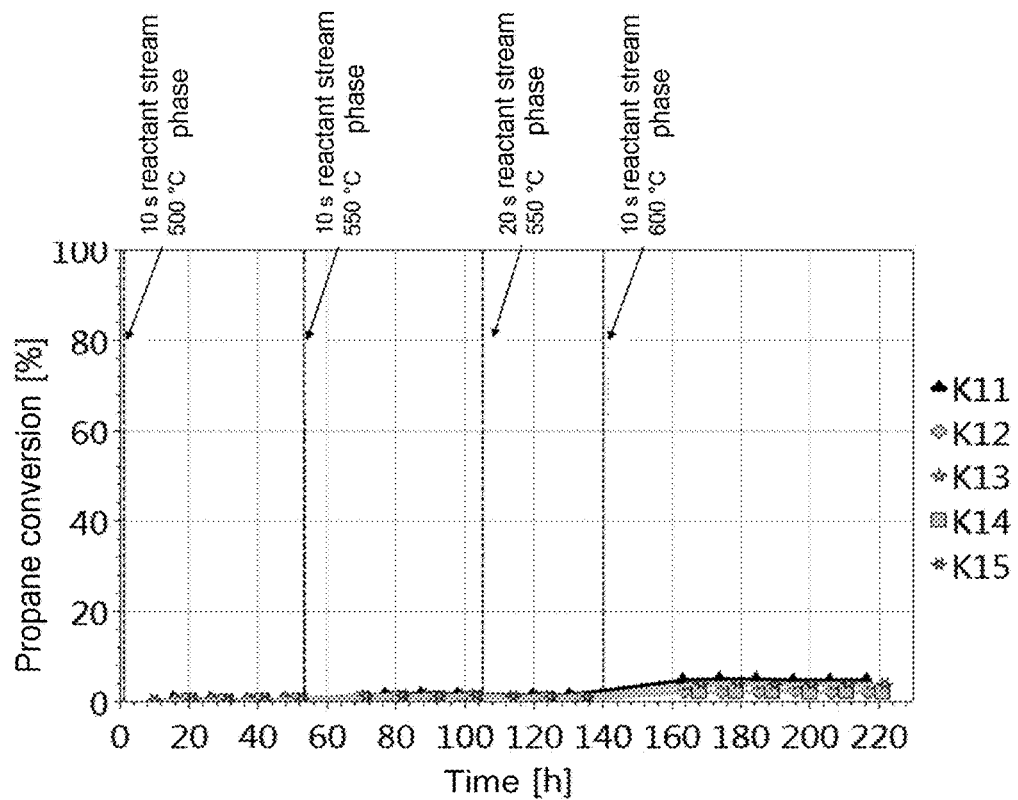
FIG. 18 shows the plot of the propane conversion for K11, K12, K13, K14 and K15 against time with the reaction parameters listed in table 7.
Figure 19:
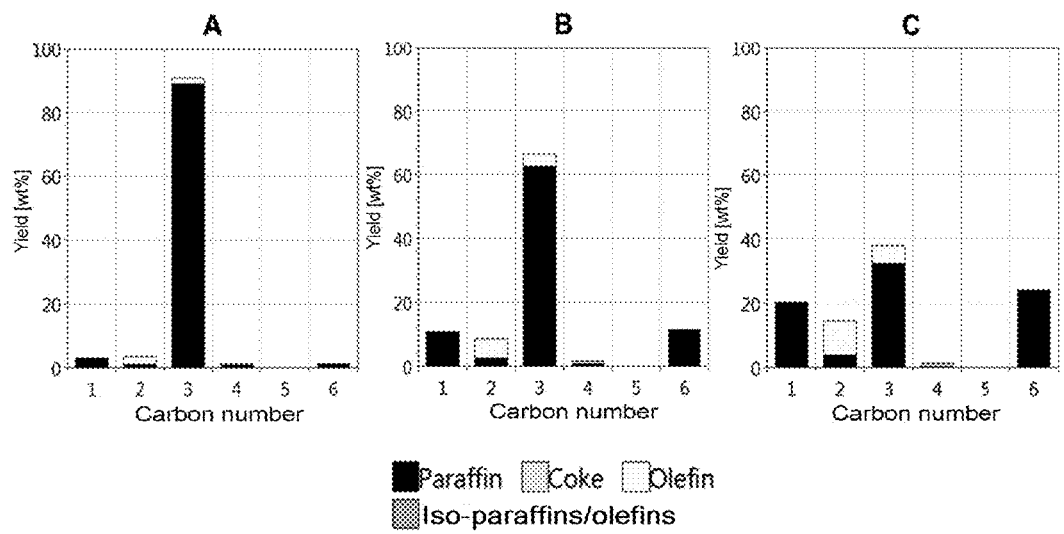
FIG. 19 shows the product distribution for K1 at 500° C. (A), 550° C. (B) and 600° C. (C) for the respective first measurement point at the particular temperature.
Figure 20:
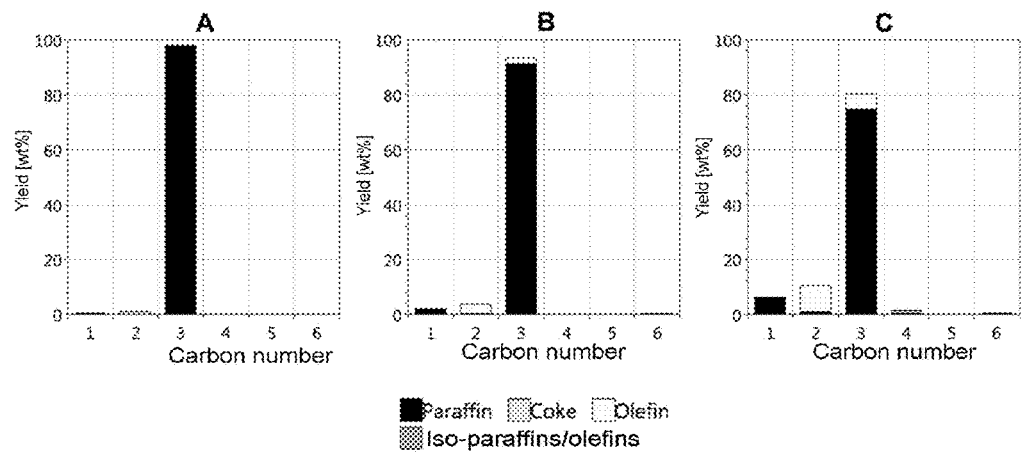
FIG. 20 shows the product distribution for K6 at 500° C. (A), 550° C. (B) and 600° C. (C) for the respective first measurement point at the particular temperature.
Figure 21:
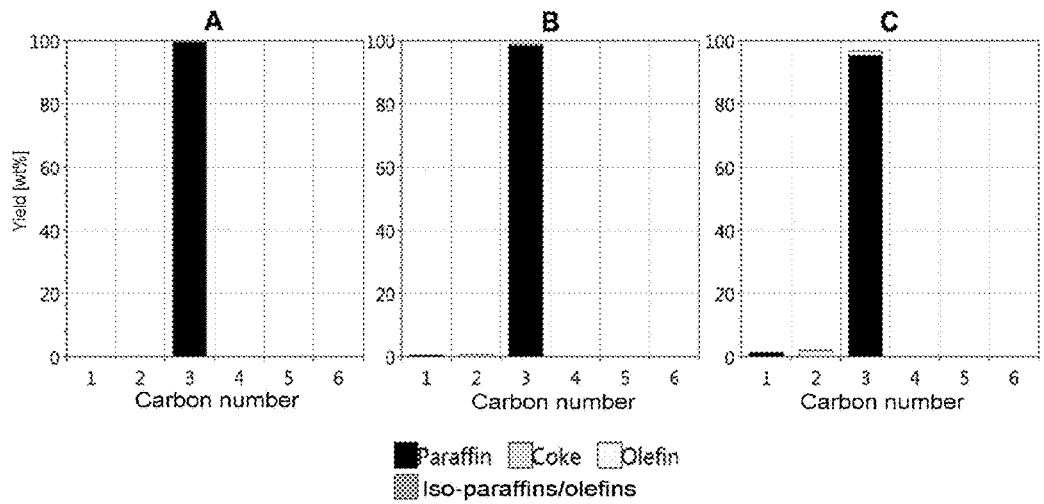
FIG. 21 shows the product distribution for K11 at 500° C. (A), 550° C. (B) and 600° C. (C) for the respective first measurement point at the particular temperature.
Figure 22:
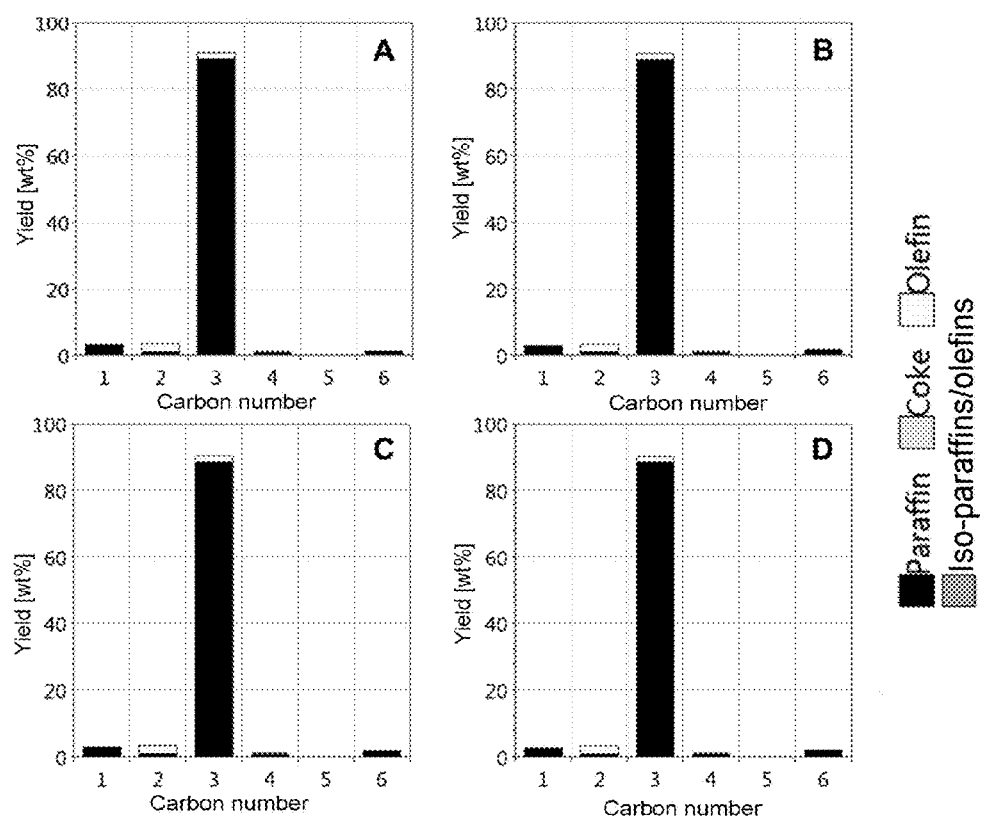
FIG. 22 shows the product distribution for K1 at 500° C. at time 11.3 h (A), 22.0 h (B), 32.6 h (C), 43.2 h (D).
Figure 23:
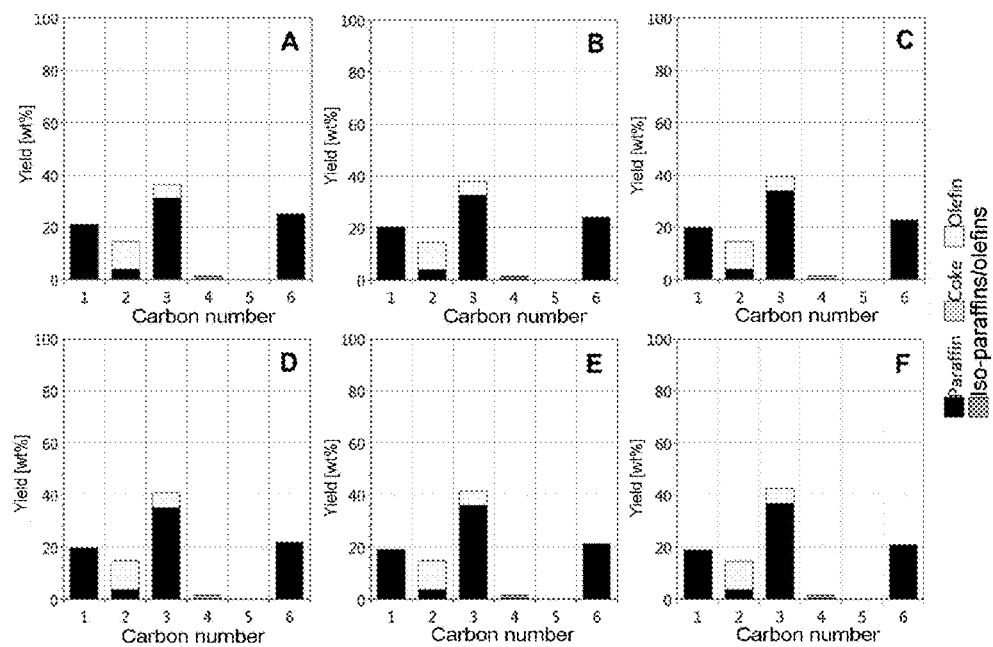
FIG. 23 shows the product distribution for K1 bei 600° C. at time 159.1 h (A), 169.8 h (B), 180.5 h (C), 191.1 h (D), 201.7 h (E), 212.4 h (F).

It should be noted in connection with the list of reference numerals and the numbering of the reference numerals that one aspect of the invention also relates to the parallelization of the apparatus and the method since this can further enhance efficiency. In order to appropriately account for the components arranged in parallel, some of the reference numerals were appended with additions comprising a division mark and a number or the letter x. The manner in which this system is to be understood should be evident to those skilled in the art from the context. It is noted that an appendage of /x means that two or more components arranged in parallel can be concerned. Consecutive numbering with the numerals /1, /2, /3 . . . means that the first, the second, the third component . . . respectively are concerned. The number of components in question depends on the degree of parallelization.

The number of multiport valves used arises from the number of feed line connections on the particular type of valve used and these feed line connections can differ with respect to feed lines and technical specifications. However, the degree of parallelization of the apparatus should also be taken into account here, since the number of required feed lines to the multiport valve also arises from the number of reactors. A sequential arrangement of mixing vessels is denoted by the following numbering [(33/x'), (33/x") . . . ], wherein (33/x') refers to the first element and (33/x") refers to the second element of the sequential arrangement. The connecting lines (22) between the components may have the same or different configurations. In the case of connecting lines having different configurations, these are then identified by (22/x). Preferably, the connecting lines have the same configuration.

LIST OF REFERENCE NUMERALS

01—Reactant fluid supply point
02—Gas supply apparatus
02/1, 02/2—Gas supply apparatus
11 Throttle element (restrictor element, for example capillary)
11/1, 11/2, . . . Throttle element 1, throttle element 2, . . . ((11/x) respectively)
21—Reaction space
21/1, 21/2, . . . Reaction space 1, reaction space 2, . . . ((21/x) respectively)
22—Connecting line from reaction space outlet with gas mixing vessel; in apparatuses with parallel design, the connecting lines (22) may have the same or different configurations
23 Connecting line from reaction space outlet to fluid vessel (24) fluid vessel 1, fluid vessel 2, . . . (or (24/x))
24/1, 24/2 Fluid vessel 1, fluid vessel 2, . . . (or (24/x))
25 Connecting line from fluid vessel (24) to substream line (36)
33—Fluid/gas mixing space, gas mixing vessel
33/1, 33/2, . . . —Fluid/gas mixing space 1, fluid/gas mixing space 2, . . . ((33/x) respectively)
36 Substream line, sidestream line
36/1, 36/2 Substream line 1, substream line 2, . . . ((36/x) respectively)
41—Multiport valve
41/1—Multiport valve 1
41/2—Multiport valve 2
42—Connecting line from multiport valve to analyzer
43—Analyzer
43/1—Analyzer 1
43/2—Analyzer 2
45→Exit air line from multiport valve
51—Control valve
62—Exit air line from analyzer 43/1
63—Exit air line from control valve
64—Exit air line from fluid supply apparatus
71—Gas supply apparatus for fluid component A
72—Gas supply apparatus for fluid component B
81—Valve 1
82—Valve 2
83—Valve 3
83/1, 83/2—Valve 3

The invention claimed is:

1. An apparatus suitable for investigating solid catalysts and processes in which discontinuous fluid streams arise, the apparatus comprising:
a reactant fluid supply point;
at least one reaction space;
at least one fluid mixing space;
at least one throttle element;
at least one pressure control valve; and
at least one analyzer,
wherein an outlet side of the at least one reaction space is connected to a connecting line, and an end of the connecting line is separated into a substream line and an exit line such that the outlet side of the at least one reaction space is operatively connected to the at least one fluid mixing space via the connecting line and the substream line and to an exit air line via the connecting line and the exit line,
the at least one fluid mixing space is connected to the at least one throttle element,
the at least one throttle element is operatively connected to the at least one analyzer and an outlet line,
the connecting line is operatively connected to the at least one pressure control valve and the exit air line, and
the at least one pressure control valve is arranged either downstream or upstream of the substream line and, when the at least one pressure control valve is upstream of the substream line, the outlet line is provided with a second pressure control valve and a pump.

2. The apparatus of claim 1, wherein the apparatus comprises a plurality of reaction spaces and a plurality of respective fluid mixing spaces,
wherein each of the reaction spaces is connected to a respective connecting line, and an end of the respective connecting line is separated into a respective substream line and a respective exit line such that the outlet side of each of the reaction spaces is operatively connected to the respective fluid mixing space via the respective connecting line and the respective substream line, and
each of the fluid mixing spaces is operatively connected to a first multiway valve.

3. The apparatus of claim 2, wherein the first multiway valve is connected to a first multiport outlet line such that each of the substream lines is operatively connected to the first multiport outlet line.

4. The apparatus of claim 2, wherein each of the substream lines is operatively connected to a second multiway valve, the second multiway valve is operatively connected to a second multiport outlet line and to a second analyzer, and the second multiway valve, the second multiport outlet line, and the second analyzer are upstream of the at least one pressure control valve.

5. The apparatus of claim 2, further comprising:
a plurality of switching valves each provided on the respective substream line between each of the reaction spaces and the respective fluid mixing space.

6. The apparatus of claim 1, wherein the at least one reaction space has an internal volume in a range of 0.5-500 mL, and the at least one fluid mixing space has an internal volume in a range of 5-5000 mL.

7. The apparatus of claim 1, further comprising:
a switching valve on the substream line between the at least one reaction space and the at least one fluid mixing space.

8. The apparatus of claim 1, wherein the apparatus comprises at least two sequentially arranged fluid mixing spaces per one reaction space, the outlet side of the at least one reaction space is operatively connected to one of the fluid mixing spaces, and an outlet side of another one of the fluid mixing spaces is operatively connected to a first multiway valve.

9. The apparatus of claim 1, wherein the at least one pressure control valve is arranged downstream of the substream line.

10. The apparatus of claim 1, wherein the at least one pressure control valve is arranged upstream of the substream line.

11. The apparatus of claim 1, wherein the apparatus comprises a plurality of reaction spaces and a plurality of respective fluid mixing spaces,
wherein each of the reaction spaces is connected to a respective connecting line, and an end of the respective connecting line is separated into a respective substream line and a respective exit line such that the outlet side of each of the reaction spaces is operatively connected to the respective fluid mixing space via the respective connecting line and the respective substream line,
each of the fluid mixing spaces is operatively connected to a first multiway valve, and each of the exit lines is operatively connected to a second multiway valve.

12. A method for characterizing discontinuous fluid streams with the apparatus of claim 1, the method comprising:
   (i) supplying a fluid stream into an interior of the at least one fluid mixing space in a controlled manner;
   (ii) commixing the fluid stream in the at least one fluid mixing space;
   (iii) transferring the commixed fluid stream to a fluid stream outlet via a conduit element; and
   (iv) withdrawing the commixed fluid stream from the conduit element and supplying a substream of the commixed fluid stream to the at least one analyzer.

13. The method of claim 12, wherein a mean retention time of a molecule or a component in the at least one fluid mixing space corresponds to at least a duration of a single cycle in which the commixed fluid stream is transferred into the at least one fluid mixing space.

14. The method of claim 13, wherein the single cycle comprises at least two alternate fluid stream phases.

15. The method of claim 14, wherein a duration of a single fluid stream phase is in a range of 0.1-3600 s.

16. The method of claim 13, wherein the duration of a single cycle is in a range from 0.2 to 7200 s.

17. The method of claim 12, wherein the fluid stream originates from a catalyst test apparatus configured to investigate a catalytic process and is a gaseous fluid stream having a GHSV in a range of 250-200,000 $h^{-1}$.

18. The method of claim 17, wherein the gaseous fluid stream is at a pressure in a range of 0.5-200 bar, and the at least one fluid mixing space is operated at a temperature in a range of 0–400° C.

19. An apparatus suitable for investigating solid catalysts and processes in which discontinuous fluid streams arise, the apparatus comprising:
   a reactant fluid supply point;
   at least one reaction space;
   at least one fluid mixing space;
   at least one throttle element;
   at least one pressure control valve; and
   at least one analyzer,
   wherein an outlet side of the at least one reaction space is connected to an arrangement comprising a first connecting line, a second connecting line, and a fluid vessel between the first and second connecting lines, and an end of the second connecting line of the arrangement is separated into a substream line and an exit line such that the outlet side of the at least one reaction space is operatively connected to the at least one fluid mixing space via the first connecting line, the fluid vessel, the second connecting line, and the substream line and to an exit air line via the first connecting line, the fluid vessel, the second connecting line, and the exit line,
   the at least one fluid mixing space is connected to the at least one throttle element,
   the at least one throttle element is operatively connected to the at least one analyzer and an outlet line,
   the second connecting line is operatively connected to the at least one pressure control valve and the exit air line, and
   the at least one pressure control valve is arranged either downstream or upstream of the substream line and, when the at least one pressure control valve is upstream of the substream line, the outlet line is provided with a second pressure control valve and a pump.

\* \* \* \* \*